US010385387B2

(12) United States Patent
Lee et al.

(10) Patent No.: US 10,385,387 B2
(45) Date of Patent: Aug. 20, 2019

(54) METHODS FOR SELECTIVELY AMPLIFYING AND TAGGING NUCLEIC ACIDS

(71) Applicant: Pacific Biosciences of California, Inc., Menlo Park, CA (US)

(72) Inventors: Walter Lee, Campbell, CA (US); Tyson Bowen, Union City, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 430 days.

(21) Appl. No.: 15/131,906

(22) Filed: Apr. 18, 2016

(65) Prior Publication Data

US 2016/0304948 A1    Oct. 20, 2016

Related U.S. Application Data

(60) Provisional application No. 62/150,193, filed on Apr. 20, 2015.

(51) Int. Cl.
| | | |
|---|---|---|
| *C12P 19/34* | (2006.01) | |
| *C12Q 1/6855* | (2018.01) | |
| *C12Q 1/6844* | (2018.01) | |

(52) U.S. Cl.
CPC ......... *C12Q 1/6855* (2013.01); *C12Q 1/6844* (2013.01)

(58) Field of Classification Search
CPC ................ C12Q 1/6844; C12Q 1/6855; C12Q 2521/319; C12Q 2525/191; C12Q 2525/301; C12Q 2565/514
USPC ........................................................ 435/91.2
See application file for complete search history.

(56) References Cited

U.S. PATENT DOCUMENTS

| | | | |
|---|---|---|---|
| 7,033,764 | B2 | 4/2006 | Korlach et al. |
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 8,153,375 | B2 | 4/2012 | Travers et al. |
| 8,586,310 | B2 | 11/2013 | Mitra et al. |
| 8,658,364 | B2 | 2/2014 | Pham et al. |
| 8,691,509 | B2 | 4/2014 | May et al. |
| 9,080,210 | B2 | 7/2015 | Van Eijk et al. |
| 9,080,211 | B2 | 7/2015 | Grunenwald et al. |
| 2010/0273219 | A1 | 10/2010 | May et al. |
| 2011/0092387 | A1 | 4/2011 | Monforte |
| 2014/0080728 | A1* | 3/2014 | Nelson ............... C12N 15/1065 506/9 |
| 2016/0340746 | A1* | 11/2016 | Makarov .............. C12Q 1/6855 |

FOREIGN PATENT DOCUMENTS

| | | |
|---|---|---|
| WO | 2006023919 A2 | 3/2006 |
| WO | 2007024798 A2 | 3/2007 |
| WO | 2007044091 A2 | 4/2007 |
| WO | 2012112804 A1 | 8/2012 |
| WO | 2012162267 A2 | 11/2012 |

OTHER PUBLICATIONS

Jr Harting, https://github.conn/PacificBiosciences/Bioinfornnatics-Training/wiki/bBarcoding-with-SMRT-Analysis-2.3, pp. 1-6, Oct. 16, 2014.*
Westerink et al., Human Immunology, 76, p. 215, Abstract LBP07, Mar. 25, 2015.*
Adey and Shendure, "Ultra-Low-Input, Tagmentation-Base Whole-Genome Bisulfite Sequencing," Genome Res. (2012) 22(6):1139-43.
Adey et al., "Rapid, Low-Input, Low-Bias Construction of Shotgun Fragment Librariues by High-Density in Vitro Transportation," Genome Biol. (2010) 11(12):R119.
Binladen et al, "The Use of Coded PCR Primers Enables High-Throughput Sequencing of Multiple Homolog Amplification Products by 454 Parallel Sequencing" PLOS ONE (2007) 2(2): e197.
Bybee et al, "Targeted amplicon sequencing (TAS): a scalable next-gen approach to multilocus, multitaxa phylogenetics" Genome Biol Evol. (2011) 2011;3:1312-23.
Harismendy and Frazer, "Method for improving sequence coverage uniformity of targeted genomic intervals amplified by LR-PCR using Illumina GA sequencing-by-synthesis technology" Biotechniques (2009) 46(3):229-31.
Hayden et al, "Multiplex-ready PCR: A new method for multiplexed SSR and SNP genotyping" BMC Genomics (2008) 9:80.
Neilan et al, "A universal procedure for primer labelling of amplicons" Nucleic Acids Res. (1997) 25(14):2938-9.
Picelli et al, "Tn5 transposase and tagmentatgion procedures for massively scaled sequencing projects" Genome Res. (2014) 24: 2033-2040.
Travers et al., A Flexible and Efficient Template Format for Circular Consensus Sequencing and SNP Detection, Nucl. Acids Res. (2010) 38(15):e159.
Transcriptome Analysis from Single Cells, Enabled by SMARTer Technology. Kit info [online]. Clontech, 11.14 IN (633066), 2014 [retrieved on Jan. 26, 2015]. Retrieved from the Internet: www.clontech.com.

(Continued)

*Primary Examiner* — Cynthia B Wilder
(74) *Attorney, Agent, or Firm* — Monicia Elrod-Erickson

(57) ABSTRACT

Methods for adding sequence tags during amplification of a nucleic acid target are provided. The target is amplified using two sets of primers that are modified such that only tagged targets can ligate to hairpin adapters that protect them from subsequent exonuclease treatment. Methods of making circular nucleic acids are also provided. Specific overhangs are created by exonuclease trimming with a polymerase such that only desired targets can ligate to sticky ended hairpin adapters that protect them from subsequent exonuclease treatment. Compositions, kits, and systems related to or useful in the methods are also described.

16 Claims, 9 Drawing Sheets

Specification includes a Sequence Listing.

(56) References Cited

OTHER PUBLICATIONS

Access Array™ Amplicon Sequencing on the Ion Torrent PGM™ Sequencer. Data sheet [online]. Fluidigm, Pub. No. 100-4903 A1 Feb. 2012 [retrieved on Jun. 20, 2016]. Retrieved from the Internet: www.fluidigm.com.

Guidelines for Using PacBio® Barcodes for SMRT® Sequencing. SampleNet-Shared protocol [online]. Pacific Biosciences, 2014 [retrieved on Aug. 18, 2015]. Retrieved from the Internet: www.pacb.com.

MASTR™ Assays Increasing Output and Reducing Workload with Massively Parallel Sequencing Technologies. Brochure [online]. Multiplicom [retrieved on Oct. 2, 2014]. Retrieved from the Internet: www.multiplicom.com.

Ligation Independent Cloning (LLC). [online]. New England BioLabs, [retrieved on Nov. 8, 2018]. Retrieved from the Internet: www.neb.com/applications/cloning-and-synthetic-biology/ligation-independent-cloning.

Nextera DNA Library Preparation Kits. Data Sheet [online]. Illumina, Pub. No. 770-2011-21, Current as of Jan. 7, 2016, [retrieved on Jun. 30, 2016]. Retrieved from the Internet: www.illumina.com/content/dam/illumina-marketing/documents/products/datasheets/datasheet_nextera_dna_sample_prep.pdf.

RainDance Technologies DeepSeq™ FFPE Solution. Data Sheet [online]. Raindance, Pub 1170006 01/11, [retrieved on Jun. 28, 2016]. Retrieved from the Internet: www.raindancetech.com/rdt/wp-content/uploads/downloads/product-brief_deepseq.pdf.

Custom Oligonucleotide Modifications Guide. [online] Sigma-Aldrich, pp. 1-45. [retrieved on Mar. 23, 2015] Retrieved from the Internet: www.sigma-aldrich.com (document submitted in 2 parts, Part I and Part II).

\* cited by examiner

SEQUENCE LISTING

<160> NUMBER OF SEQ ID NOS: 1

<210> SEQ ID NO 1
<211> LENGTH: 30
<212> TYPE: DNA
<213> ORGANISM: Artificial Sequence
<220> FEATURE:
<223> OTHER INFORMATION: labeled synthetic oligonucleotide

<400> SEQUENCE: 1
ttgatcgcag agtcatgtat agttaggcgc                                    30

METHODS FOR SELECTIVELY AMPLIFYING AND TAGGING NUCLEIC ACIDS

CROSS-REFERENCE TO RELATED APPLICATIONS

This application is a non-provisional utility patent application claiming priority to and benefit of the following prior provisional patent application: U.S. Ser. No. 62/150,193, filed Apr. 20, 2015, entitled "Methods for Selectively Amplifying and Tagging Nucleic Acids" by Walter Lee and Tyson Bowen, which is incorporated herein by reference in its entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 1 KB file (01018601_2016-06-30_SequenceListing.txt).

FIELD OF THE INVENTION

The invention relates to methods of selectively amplifying nucleic acid targets and tagging them with identifiable nucleotide sequences.

BACKGROUND OF THE INVENTION

Nucleic acid amplification is widely employed to produce sufficient starting material for techniques such as DNA cloning, nucleic acid sequencing, and the like. Amplified nucleic acid products are employed in numerous research, medical, and food and environmental monitoring techniques, as well as in many similar applications. In such techniques, particularly techniques in which large numbers of samples are handled, amplified nucleic acids are desirably tagged with unique, identifiable sequences generally known as barcodes or multiple identifiers. Such tags enable the pooling of amplified products to simplify handling while maintaining the ability to uniquely identify a particular product, for example, through its linkage to a tag associated with the originating sample source.

Methods for introducing sequence tags into amplified target nucleic acids are thus desirable. The present invention meets these and other needs by providing, inter alia, methods of amplifying and tagging target nucleic acids. A complete understanding of the invention will be obtained upon review of the following.

SUMMARY OF THE INVENTION

The present invention provides methods of amplifying and tagging nucleic acids, as well as methods for making circular nucleic acids.

One general class of embodiments provides methods for amplifying and tagging a target nucleic acid. In the methods, an amplification mixture is prepared comprising a nucleic acid comprising a target region, a forward internal primer comprising a first universal sequence and a first target-specific sequence, a reverse internal primer comprising a second universal sequence and a second target-specific sequence, a forward external primer comprising the first universal sequence and a first tag sequence, and a reverse external primer comprising the second universal sequence and an optional second tag sequence. The first and second target-specific sequences anneal to sites in the nucleic acid that flank the target region on opposite strands. The amplification mixture is subjected to amplification to produce a mixture of nucleic acid products. Those nucleic acid products in the product mixture into which both a forward external primer and a reverse external primer were not incorporated are selectively degraded. The nucleic acid product into which both a forward external primer and a reverse external primer were incorporated is protected from degradation.

In one class of embodiments, ligation of two stem-loop adapters to the nucleic acid product into which both a forward external primer and a reverse external primer were incorporated protects it from degradation. Other nucleic acid products, into which both a forward external primer and a reverse external primer were not incorporated, can be selectively degraded by treating the product mixture with one or more exonucleases to digest nucleic acid products having one or no stem-loop adapter ligated thereto. Various strategies can be employed to ensure that only the desired tagged product is capable of ligating to two stem-loop adapters. In one class of embodiments, the forward and reverse internal primers are 5' blocked. In a 5' blocked primer, the presence of a blocking group at the 5' terminus of the primer prevents the 5' end of the primer from participating in a ligation reaction. In another class of embodiments, the forward and reverse internal primers lack a free 5' phosphate group, and the forward and reverse external primers comprise a free 5' phosphate group.

The methods can be used to amplify and tag nucleic acids for any of a variety of applications. For example, the methods can include determining a polynucleotide sequence of the target region, the first tag sequence, and the optional second tag sequence from the product after the selective degradation step.

The methods are suitable for tagging large numbers of nucleic acids, for example, in highly multiplexed or high throughput applications. As just one example, the methods can be applied to tagging and subsequent analysis of a given target from a number of different sources. Thus, in one exemplary class of embodiments, the methods include preparing multiple amplification mixtures. Different amplification mixtures comprise a nucleic acid comprising the same target region from different sources. Different amplification mixtures include the same pair of forward and reverse internal primers but different pairs of forward and reverse external primers; the forward and reverse external primers in different mixtures include the same first and second universal sequences but different first and optional second tag sequences, where the tag sequences uniquely identify the source for each of the nucleic acids.

The amplification mixtures are subjected to amplification. Typically, the resulting mixtures of nucleic acid products are then pooled to provide a pooled product mixture, and those nucleic acid products in the pooled product mixture into which both a forward external primer and a reverse external primer were not incorporated are selectively degraded (e.g., by ligation and exonuclease treatment as noted above). The resulting products can be subjected to further analysis. For example, the polynucleotide sequence of the target region, the first tag sequence, and the optional second tag sequence can be determined for multiple products.

In embodiments in which the reverse external primer comprises a second tag sequence, the first and second tag sequences can comprise different polynucleotide sequences, or they can comprise the same polynucleotide sequence. In one class of embodiments, the tag sequences in the forward and reverse external primers are reverse complements. Similarly, the first and second universal sequences can comprise the same polynucleotide sequence, or they can comprise different polynucleotide sequences.

Another general class of embodiments provides methods for amplifying and tagging a target nucleic acid. In the methods, a first amplification mixture is prepared that includes a nucleic acid comprising a target region, a forward internal primer comprising a first universal sequence and a first target-specific sequence, and a reverse internal primer comprising a second universal sequence and a second target-specific sequence. The first and second target-specific sequences anneal to sites in the nucleic acid that flank the target region on opposite strands. The forward and reverse internal primers are 5' blocked. The first amplification mixture is subjected to amplification to produce a 5' blocked intermediate product.

A second amplification mixture is then prepared comprising the intermediate product, a forward external primer comprising the first universal sequence and a first tag sequence, and a reverse external primer comprising the second universal sequence and an optional second tag sequence. The second amplification mixture is subjected to amplification to produce a tagged product. Two stem-loop adapters are ligated to the ends of the tagged product to produce a circular nucleic acid. The circular nucleic acid is exposed to one or more exonucleases that selectively degrade any single-stranded or non-circular double-stranded nucleic acid present (for example, the blocked intermediate product which cannot ligate to the adapters) but do not degrade the circular nucleic acid.

The methods can be used to amplify and tag nucleic acids for any of a variety of applications. For example, the methods can include determining a polynucleotide sequence of the target region, the first tag sequence, and the optional second tag sequence from the product after the selective degradation step.

The methods are suitable for tagging large numbers of nucleic acids, for example, in highly multiplexed or high throughput applications. As just one example, the methods can be applied to tagging and subsequent analysis of a given target from a number of different sources. Thus, in one exemplary class of embodiments, the methods include preparing multiple first and second amplification mixtures. Different first amplification mixtures comprise a nucleic acid comprising the same target region from different sources and the same forward and reverse internal primers. Different second amplification mixtures comprise forward and reverse external primers comprising the same first and second universal sequences but different first and optional second tag sequences, which uniquely identify the source for each of the nucleic acids. After the first and second amplification mixtures are subjected to amplification, the resulting tagged products are typically pooled prior to the ligation and selective degradation steps. The resulting circular nucleic acids can be subjected to further analysis. For example, the polynucleotide sequence of the target region, the first tag sequence, and the optional second tag sequence can be determined for multiple circular nucleic acids.

In embodiments in which the reverse external primer comprises a second tag sequence, the first and second tag sequences can comprise different polynucleotide sequences, or they can comprise the same polynucleotide sequence. In one class of embodiments, the tag sequences in the forward and reverse external primers are reverse complements. Similarly, the first and second universal sequences can comprise the same polynucleotide sequence, or they can comprise different polynucleotide sequences.

Another general class of embodiments provides methods of making a circular nucleic acid. In the methods, a double-stranded nucleic acid comprising a target region is provided. The double-stranded nucleic acid is treated with an enzyme having polymerase activity and 3'→5' exonuclease activity, in the presence of at most three types of dNTPs (preferably in the presence of a single type of dNTP), to produce a sticky-ended product having 5' overhangs. A first stem-loop adapter is ligated to one end of the sticky-ended product and a second stem-loop adapter is ligated to the other end of the sticky-ended product to produce a circular nucleic acid. The resulting circular nucleic acid is exposed to one or more exonucleases, which selectively degrade any single-stranded or non-circular double-stranded nucleic acid present but do not degrade the circular nucleic acid.

The double-stranded nucleic acid can be prepared using essentially any convenient technique. For example, in one class of embodiments, the double-stranded nucleic acid is provided by exposing a nucleic acid sample comprising the target region (e.g., a sample of genomic DNA) to a transposase and to at least one adapter that comprises a transposon end sequence, under conditions wherein a transposition reaction is catalyzed by the transposase. In another exemplary class of embodiments, the double-stranded nucleic acid is provided by amplifying the target nucleic acid region.

A related general class of embodiments provides methods of making a circular nucleic acid. In the methods, a target nucleic acid region is amplified to provide a double-stranded product, typically a product having blunt ends or 3'-overhangs. The double-stranded product is treated with an enzyme having polymerase activity and 3'→5' exonuclease activity, in the presence of at most three types of dNTPs (preferably in the presence of a single type of dNTP), to produce a sticky-ended product having 5' overhangs. A first stem-loop adapter is ligated to one end of the sticky-ended product and a second stem-loop adapter is ligated to the other end of the sticky-ended product to produce a circular nucleic acid. The resulting circular nucleic acid is exposed to one or more exonucleases, which selectively degrade any single-stranded or non-circular double-stranded nucleic acid present but do not degrade the circular nucleic acid.

In one class of embodiments, the two 5' overhangs on the sticky-ended product have different polynucleotide sequences, and the first stem-loop adapter has a 5' overhang complementary to one of the overhangs on the product and the second stem-loop adapter has a 5' overhang complementary to the other overhang on the product. In another class of embodiments, the two 5' overhangs on the sticky-ended product have the same polynucleotide sequence, and the first and second stem-loop adapter (which are optionally identical to each other) each have a 5' overhang complementary to the overhang on the product. The 5' overhangs on the sticky-ended product (and the complementary overhangs on the adapters) can be of essentially any convenient length. For example, the 5' overhangs on the sticky-ended product can be between 4 and 12 nucleotides in length.

The target nucleic acid region can be amplified by essentially any convenient technique, e.g., PCR. The primers employed for the amplification are preferably designed to produce overhangs of the desired sequence. Thus, in one class of embodiments, the target nucleic acid region is amplified using a forward primer comprising a first end sequence and at least one stop base and a reverse primer comprising a second end sequence and at least one stop base. The end sequences are located at the 5' end of the primers and are immediately followed by the stop bases. No nucleotide in the first and second end sequences is complementary to any of the dNTPs present in the treating step, and each stop base is complementary to a dNTP present in the treating step.

The first and second end sequences can be identical, e.g., in embodiments in which the same type of stem-loop adapter is ligated to both ends of the resulting sticky-ended product. In other embodiments, the first and second end sequences comprise different polynucleotide sequences. The resulting 5' overhangs on the sticky ended product are thus different, and different stem-loop adapters can be ligated to the different ends.

In one class of embodiments, the target region is amplified using a single primer pair. The forward primer has a first end sequence followed by at least one stop base at its 5' end, and a first target-specific sequence at its 3' end. Similarly, the reverse primer has a second end sequence followed by at least one stop base at its 5' end, and a second target-specific sequence at its 3' end. The first and second target-specific sequences anneal to sites that flank the target region on opposite strands of the template containing the target region. One or both primers optionally include a tag sequence, typically between the stop base and the target-specific sequence. When both primers include a tag sequence, the tags can be the same or different. Optionally, the tag sequences are reverse complements.

In another class of embodiments, the target region is amplified using two pairs of primers (a pair of internal primers that add universal sequences to the target region in an intermediate product, and a pair of external primers), which can be employed sequentially in separate reactions or together in a single reaction. The forward internal primer comprises a first universal sequence and a first target-specific sequence, and the reverse internal primer comprises a second universal sequence and a second target-specific sequence. The first and second target-specific sequences anneal to sites that flank the target region on opposite strands of the template containing the target region. The forward external primer has a first end sequence followed by at least one stop base at its 5' end, and the first universal sequence, typically at its 3' end. The reverse external primer has a second end sequence followed by at least one stop base at its 5' end, and the second universal sequence, typically at its 3' end. One or both external primers optionally include a tag sequence, typically between the stop base and the universal sequence. When both of the external primers include a tag sequence, the tags can be the same or different. The first and second end sequences can be the same or different, independent of any tag sequences. For example, the first and second tag sequences can comprise different polynucleotide sequences, while the first and second end sequences comprise the same polynucleotide sequence. The forward and reverse internal primers optionally each comprise at least one stop base at their 5' end.

The methods can be used to amplify, optionally tag, and circularize nucleic acids for any of a variety of applications. For example, the methods can include determining a polynucleotide sequence of the target region (and any tag sequences) from the circular product after the selective degradation step.

The methods are suitable for circularizing (and optionally tagging) large numbers of nucleic acids, for example, in highly multiplexed or high throughput applications. As just one example, the methods can be applied to amplification, optional tagging, and subsequent analysis of a given target from a number of different sources. Thus, in one class of embodiments, the methods include amplifying the target nucleic acid region in multiple separate amplification mixtures, wherein different amplification mixtures comprise a nucleic acid comprising the same target region from different sources, and pooling the resulting double-stranded products before the treating step. The resulting circular nucleic acids can be subjected to further analysis. For example, the polynucleotide sequence of the target region and any tag sequences can be determined for multiple circular nucleic acids.

Figure 1:
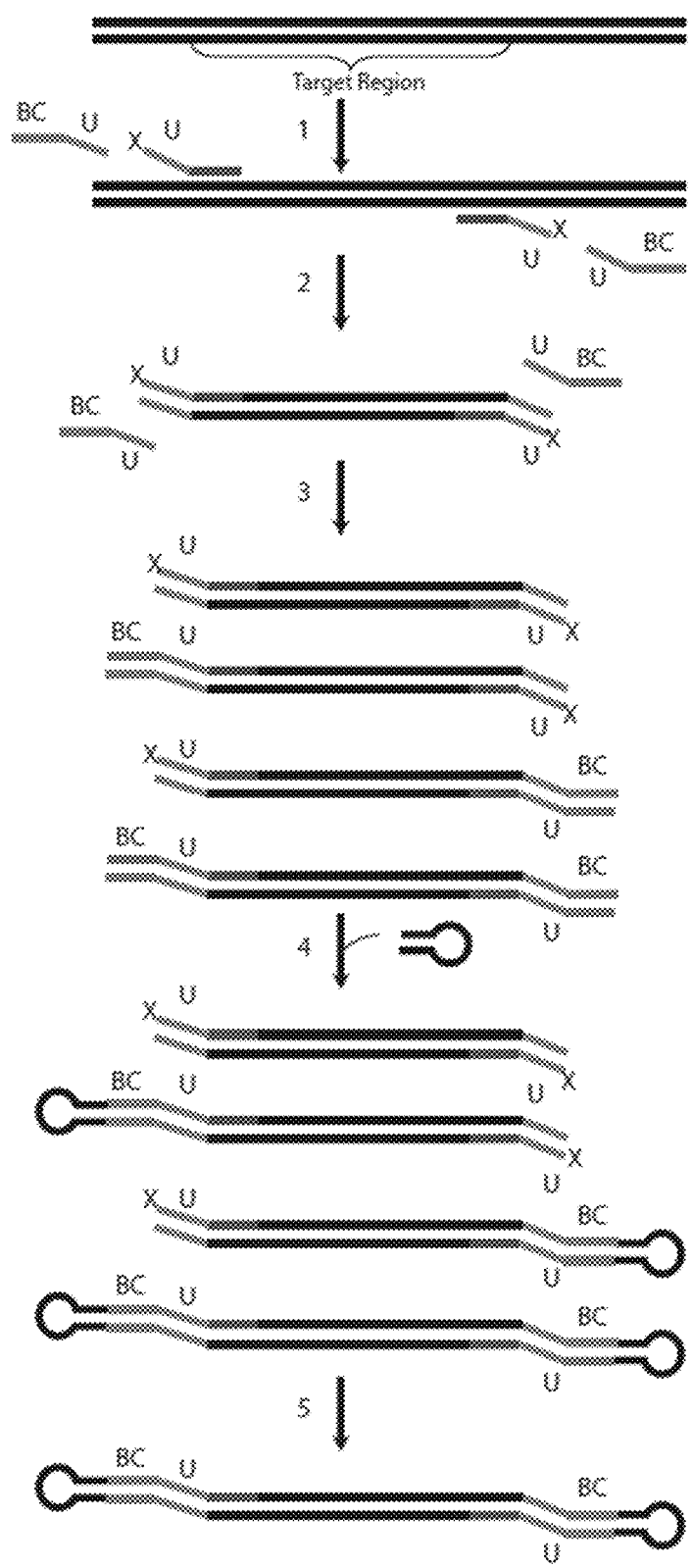
FIG. 1 schematically illustrates a method in which two internal primers and two external primers are employed in a single amplification reaction to amplify and tag a target nucleic acid region. The desired tagged target is protected from exonuclease digestion by ligation of two hairpin adapters, while other products are selectively degraded.

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an," and "the" include plural referents unless the context clearly dictates otherwise. Thus, for example, reference to "a protein" includes a plurality of proteins, reference to "a cell" includes mixtures of cells, and the like.

"Amplification" as used herein encompasses any means by which at least a part of at least one target nucleic acid is reproduced, typically in a template-dependent manner, including without limitation a broad range of techniques for amplifying nucleic acid sequences, either linearly or exponentially. Illustrative means for performing an amplifying step include polymerase chain reaction (PCR), ligase chain reaction (LCR), ligase detection reaction (LDR), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof. In some embodiments, amplification comprises at least one cycle of the sequential procedures of: denaturing double-stranded nucleic acids to separate the strands; annealing at least one primer with complementary or substantially complementary sequences to at least one target nucleic acid; and synthesizing at least one strand of nucleotides in a template-dependent manner using a polymerase. The cycle may or may not be repeated. Amplification can comprise thermocycling or can be performed isothermally.

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches. "Complementary" can also refer to the capacity for precise pairing between two nucleotides, for example, G with C and A with T (or U).

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra. "Specific hybridization" or "specific annealing" refers to the binding of a nucleic acid to a target nucleotide sequence in the absence of substantial binding to other nucleotide sequences present in the hybridization mixture under defined stringency conditions.

The terms "nucleic acid," "polynucleotide," and "oligonucleotide" encompasses any physical string of monomer units that can be corresponded to a string of nucleotides, including a polymer of nucleotides (e.g., a typical DNA or RNA polymer), PNAs, modified oligonucleotides (e.g., oligonucleotides comprising nucleotides that are not typical to biological RNA or DNA, such as 2'-O-methylated oligonucleotides, and/or alternate backbones, e.g., including non-phosphodiester bonds), and the like. A nucleic acid can be e.g., single-stranded or double-stranded. Unless otherwise indicated, a particular nucleic acid sequence of this invention encompasses complementary sequences, in addition to the sequence explicitly indicated.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "primer" refers to an oligonucleotide that is capable of hybridizing (also termed "annealing") with a nucleic acid and serving as an initiation site for nucleotide (RNA or DNA) polymerization under appropriate conditions (e.g., in the presence of four different nucleoside triphosphates and an agent for polymerization, such as DNA or RNA polymerase or reverse transcriptase) in an appropriate buffer and at a suitable temperature. A primer is said to anneal to another nucleic acid if the primer, or a portion thereof, hybridizes to a nucleotide sequence within the nucleic acid. It will be understood that certain bases (e.g., the 3' base of a primer) are generally desirably perfectly complementary to corresponding bases of the template nucleic acid sequence.

The term "primer pair" refers to a set of primers including a "forward primer" that hybridizes with the complement of the 5' end of a DNA sequence to be amplified and a "reverse primer" that hybridizes with the 3' end of the sequence to be amplified. As will be recognized by those of skill in the art, the terms "forward" and "reverse" are not intended to be limiting, but rather provide illustrative orientation in particular embodiments.

The term "stem-loop adapter" refers to a hairpin oligonucleotide comprising a single-stranded loop closed by a double-stranded stem. The adapter (i.e., the stem) can be blunt ended or can have a single-stranded overhang (e.g., a 5' overhang).

The term "tag sequence" is used herein to refer to a predetermined nucleotide sequence that is added to a target nucleotide sequence. The nucleotide tag can encode an item of information about the target nucleotide sequence, such as the identity of the target nucleotide sequence or the identity of the sample from which the target nucleotide sequence was derived. In certain embodiments, such information may be encoded in one or more nucleotide tags; for example, a combination of two nucleotide tags, one on either end of a target nucleotide sequence, can encode the source of the target nucleotide sequence.

As used herein with reference to a portion of a primer, the term "target-specific sequence" refers to a sequence that can specifically anneal to a target nucleic acid region under suitable annealing conditions.

The term "universal sequence" is used herein to refer to a predetermined nucleotide sequence that is added to a target nucleotide sequence, typically to facilitate its amplification.

Where a range of values is provided, it is understood that each intervening value between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

A variety of additional terms are defined or otherwise characterized herein.

DETAILED DESCRIPTION

Sequence tags (also known in the art as barcodes or multiple identifiers) are predetermined polynucleotide sequences that can be added to nucleic acids of interest to encode information about those nucleic acids. For example, a unique sequence tag can be added to a nucleic acid amplified from a particular source. The tag can then be used to identify the source of the nucleic acid, even if the tagged nucleic acid is subsequently pooled with differently tagged nucleic acids amplified from other sources.

Use of sequence tags can facilitate high throughput analysis of large numbers of samples, for example, sequencing of a particular genomic region, cDNA, or the like from large numbers of different individuals. The target nucleic acid is amplified from each individual separately and tagged with a unique, known sequence. The tagged nucleic acids are then pooled for subsequent manipulation and sequence determination. When the resulting sequence information is analyzed, the sequence of the tag associated with a given target sequence permits identification of the individual from which that sample was initially obtained.

The present invention provides several methods for adding sequence tags during amplification of a nucleic acid target. In one aspect, the target is amplified using two sets of primers that are modified such that only tagged targets can ligate to blunt ended hairpin adapters that protect them from subsequent exonuclease treatment. In another aspect, specific overhangs are created by exonuclease trimming such that only tagged targets can ligate to sticky ended hairpin adapters that protect them from subsequent exonuclease treatment.

Amplification with Blocked Internal Primers

In one aspect, the invention provides methods for amplifying and tagging a target nucleic acid. In the methods, a desired region of a nucleic acid of interest (a "target region") is amplified and one or more sequence tags (also called barcodes) are added at one or both ends of the target region. The target region is typically amplified in two stages. In the first stage, a pair of internal primers that anneal to sites flanking the target is employed to add a universal sequence to each end of the target region. In the second stage, a pair of external primers that anneal to the universal sequences is employed to add a sequence tag to one or both ends of the target region. Although the target could be amplified and the sequence tags added in a single stage employing only one primer pair, employing two primer pairs provides greater flexibility for high throughput applications of the technique: universal sequences, sequence tags, and external primers can be designed and validated once and then employed to tag essentially any target, requiring only the design and testing of internal primers specific for that target and including the pre-tested universal sequences.

As noted, the target region is generally amplified in two stages, employing four primers. The two stages can be performed sequentially in separate reaction mixtures that each include only one of the two pairs of primers, or they can be performed in a single reaction mixture that includes both pairs of primers.

Thus, in one general class of embodiments, a first amplification mixture comprising a nucleic acid comprising the target region, a forward internal primer comprising a first universal sequence and a first target-specific sequence, and a reverse internal primer comprising a second universal sequence and a second target-specific sequence is prepared. The first and second target-specific sequences anneal to sites in the nucleic acid that flank the target region on opposite strands. It will be evident that the target-specific sequences are preferably located at the 3' end of the internal primers, for efficient extension of the primers; the universal sequences are thus generally located 5' of the target-specific sequences.

The first amplification mixture is subjected to amplification by essentially any convenient technique, e.g., PCR, to produce an intermediate product. The intermediate product comprises the target region with the first universal sequence at one end and the second universal sequence at the other end. The internal primers are optionally removed from the intermediate product, e.g., using a size-selection technique. A variety of size-selection techniques are known in the art, and many products are commercially available. Such methods include, but are not limited to, bead-, gel-, chromatography-, and density-based methods, e.g., SPRI (solid phase reversible immobilization) bead-based methods such as AMPURE SPRI bead-based methods (Beckman Coulter, Brea, Calif.).

A second amplification mixture comprising the intermediate product, a forward external primer comprising the first universal sequence and a first tag sequence, and a reverse external primer comprising the second universal sequence and an optional second tag sequence is then prepared. It will be evident that the universal sequences are preferably located at the 3' end of the external primers, for efficient extension of the primers; the tag sequences are thus generally located 5' of the universal sequences. The second amplification mixture is subjected to amplification to produce a tagged product. The tagged product includes the first tag sequence, the first universal sequence, the target region, the second universal sequence, and the optional second tag sequence.

Any nucleic acids present other than the tagged product are selectively degraded. For example, the tagged product can be protected by ligation to a pair of stem-loop adapters prior to exposure to one or more exonucleases that degrade any single-stranded nucleic acids and any double-stranded nucleic acids having a free terminal nucleotide, as described in greater detail below.

Performing the two stages in separate steps can be useful, e.g., for determining initial reaction conditions for efficient amplification of the target region. For high throughput applications, however, minimizing the number of steps by performing the two stages in a single step is typically preferred.

Accordingly, in another general class of embodiments, an amplification mixture comprising a nucleic acid comprising the target region, a forward internal primer comprising a first universal sequence and a first target-specific sequence, a reverse internal primer comprising a second universal sequence and a second target-specific sequence, a forward external primer comprising the first universal sequence and a first tag sequence, and a reverse external primer comprising the second universal sequence and an optional second tag sequence is prepared. The first and second target-specific sequences anneal to sites in the nucleic acid that flank the target region on opposite strands of the nucleic acid. As for the embodiments above, the target-specific sequences are preferably located at the 3' end of the internal primers, for efficient extension of the primers; the universal sequences are thus generally located 5' of the target-specific sequences. Similarly, the universal sequences are preferably located at the 3' end of the external primers, for efficient extension of the primers; the tag sequences are thus generally located 5' of the universal sequences.

The amplification mixture is subjected to amplification by essentially any convenient technique, e.g., PCR, to produce a mixture of nucleic acid products. See, e.g., step 3 in FIG. 1. The desired tagged product includes the first tag sequence, the first universal sequence, the target region, the second universal sequence, and the optional second tag sequence; this product has incorporated both a forward and a reverse external primer. Other products expected to be present include products into which only one of the external primers was incorporated, e.g., products having a tag sequence at only one end and a universal sequence at the other end, and a product into which neither external primer was incorporated and which therefore has a universal sequence at each end.

It will be evident that, in a one step reaction, increasing the ratio of external primers to internal primers will generally favor formation of the desired product. Thus, the ratio of external primers to internal primers is typically greater than 1:1, e.g., 3:1, 5:1, 10:1, 100:1, or even 1,000:1. Forward and reverse primers (i.e., forward and reverse internal or forward and reverse external primers) are typically provided in a ratio of about 1:1.

Whether the two stages of amplification are performed in two steps or in a single step, those nucleic acid products in the product mixture into which both a forward external primer and a reverse external primer were not incorporated are selectively degraded, while the nucleic acid product into which both a forward external primer and a reverse external primer were incorporated is protected from degradation. In one aspect, selective degradation is accomplished by protecting the termini of only the desired tagged product from exonuclease digestion. Thus, in one class of embodiments, a stem-loop adapter is ligated to each end of the desired tagged product. The resulting molecule is a circular nucleic acid having a double-stranded central region (comprising the target region, the universal sequences, the tag sequence(s) and the stems of the adapters) and two single-stranded hairpin end regions (that is, loops connecting the two complementary strands of the double-stranded region, corresponding to the loops of the adapters). As will be appreciated, the term circular, when referring to the strand configuration, merely denotes a strand of a nucleic acid that includes no terminal nucleotides, and does not necessarily denote any geometric configuration. Production of such circular nucleic acids by ligation of stem-loop adapters is described, e.g., in U.S. Pat. No. 8,153,375 "Compositions and Methods for Nucleic Acid Sequencing" and in Travers et al. (2010) Nucl. Acids Res. 38(15):e159, each of which is incorporated herein by reference in its entirety for all purposes.

The tagged product can be ligated to two different adapters, such that the resulting hairpin end regions are different, or it can be ligated to two adapters of the same type, such that the resulting hairpin end regions are the same. For example, in embodiments in which amplification is performed by a polymerase that produces blunt ended products, a single type of blunt ended stem-loop adapter can be ligated to both ends of the tagged product. As another example, when amplification is performed by a polymerase that produces 3' A overhangs, blunt ends can be produced by treating the tagged product with T4 DNA polymerase and a suitable mixture of dNTPs as is known in the art. A single type of blunt ended stem-loop adapter can then be ligated to both ends of the tagged product. As yet another example, where restriction enzyme sites are present at the ends of the tagged product (e.g., having been designed into the external primers), digestion with the appropriate enzyme(s) produces overhangs to which stem-loop adapters having complementary overhangs can be ligated. A single type of adapter can be employed where the overhangs created on the tagged product are the same, or two different adapters can be employed where the overhangs on the two ends of the product are different.

After the ligation reaction joining the stem-loop adapters to the tagged product has been performed, an exonuclease or combination of exonucleases (e.g., ExoIII and ExoVII) can be added to degrade any nucleic acids that have a free terminal nucleotide, for example, other products of the amplification reaction, to which only one or no stem-loop adapter was able to ligate. The tagged product, circularized and protected by ligation to two stem-loop adapters, has no free termini and survives the exonuclease treatment intact. The exonuclease can then be deactivated (e.g., heat killed) or removed.

Various strategies can be employed to ensure that only the desired tagged product is capable of ligating to two stem-loop adapters. In one exemplary strategy, the forward and reverse external primers comprise a free 5' phosphate group, while the forward and reverse internal primers lack a free 5' phosphate group. For example, the internal primers can have a free 5' hydroxyl group. Since the internal primers lack a free 5' phosphate group, any product ending in sequence originating from an internal primer also lacks a free 5' phosphate group and thus cannot ligate to the stem-loop adapter. Only the tagged product into which both a forward external primer and a reverse external primer were incorporated has a free 5' phosphate group at both ends and can therefore ligate to two stem-loop adapters. It will be evident that T4 polynucleotide kinase (or a similar kinase capable of transferring a phosphate to the 5' hydroxyl of the internal primers) should not be employed in such embodiments.

As another example, the forward and reverse internal primers can be 5' blocked. In a 5' blocked primer, the presence of a blocking group at the 5' terminus of the primer prevents the primer from participating in a ligation reaction with a free 3' hydroxyl. A variety of chemical modifications to the 5' terminus (e.g., to a 5' phosphate) are known in the art and are suitable for producing a 5' blocked primer. Examples include, but are not limited to, amino modifiers such as an amino C6 linker (which includes a primary amine group and a six carbon chain on the 5' phosphate), an amino C3 linker, an amino C12 linker, a biotin moiety, a C3 spacer (which includes a hydroxyl group and a three carbon spacer attached to the 5' phosphate), a C6 spacer, and polyethylene glycol spacers such as spacer 9 and spacer 18. In embodiments in which 5' blocked internal primers are employed, the external primers can bear a free 5' phosphate group, or the tagged product can be phosphorylated by treatment with T4 polynucleotide kinase or similar enzyme as is well known in the art prior to the ligation step.

An exemplary embodiment employing blocked internal primers is schematically illustrated in FIG. 1. A nucleic acid including the target region is provided as shown in step 1, as are internal and external primer pairs. Each internal primer includes a 5' blocking group (indicated by the X), a universal sequence (U), and a sequence complementary to part of the target region. Each external primer includes a universal sequence and a tag sequence (BC). As shown in step 2, amplification of the target region with the internal primer pair produces an intermediate product having a universal sequence at each end. The intermediate product also has a blocking group at both of its 5' termini. Amplification in the presence of all four primers produces a mixture of products, as shown in step 3: the intermediate product with universal sequences and 5' blocking groups at both ends, two products with a universal sequence and a 5' blocking group at one end and a tag at the other end, and the desired product with a tag at both ends. Since the desired product was produced by incorporation of both external primers, it is the only product without the 5' blocking group. The doubly tagged product is thus the only one to which two stem-loop adapters can ligate in step 4; the 5' blocking group present on the other products prevents ligation of the adapter. The desired, doubly tagged product is thus the only one to survive treatment with exonuclease, as shown in step 5. The other products, which have at least one free terminus due to the presence of the blocking group, are degraded.

The resulting circular nucleic acid product can be employed in essentially any desired application, e.g., nucleic acid sequencing, amplification, analysis, or the like. If desired, the circular nucleic acid can be fully or partially linearized, e.g., by digestion with a restriction enzyme that recognizes a site in the stem of the adapter(s). Optionally, in embodiments in which two different adapters are employed, one adapter includes the restriction enzyme recognition site and the other does not, such that digestion produces a long hairpin, optionally including a 5' overhang.

Figure 2:
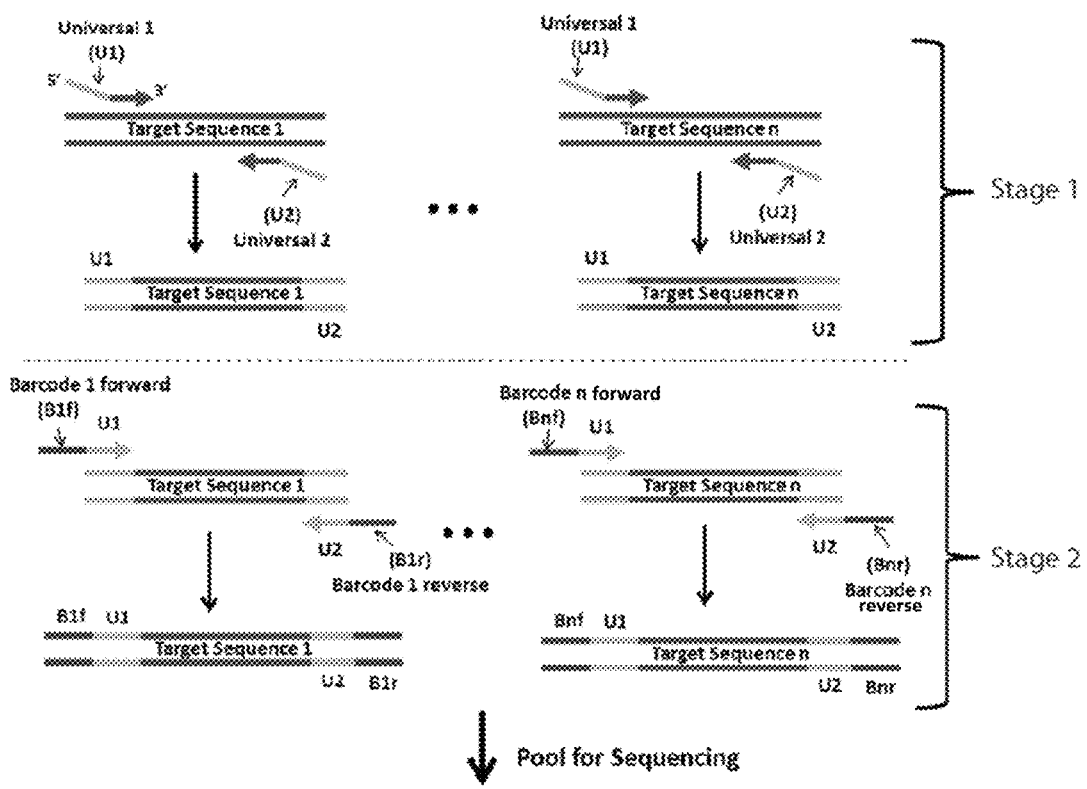
FIG. 2 schematically illustrates amplification and tagging of multiple target regions in separate reactions, after which the tagged amplified products are pooled. For each individual target, stages 1 and 2 can be performed in a single reaction or in separate reactions.

The methods are suitable for tagging large numbers of nucleic acids, for example, in highly multiplexed or high throughput applications. See, e.g., the exemplary embodiment schematically illustrated in FIG. 2. As just one example, the methods can be applied to tagging and subsequent analysis of a given target from a number of different sources (e.g., a genomic region, cDNA, or the like from multiple individuals (e.g., humans), or a pathogen-identifying target or other species-identifying target from samples obtained from multiple different locations, individuals, or batches of food or other product). Targets obtained from different sources are tagged in separate reactions. Typically, a single pair of forward and reverse internal primers is used for the first stage of amplification in all the reactions, while different forward and reverse external primer pairs are employed for the second stage of amplification. The forward and reverse external primers typically all include the same first and second universal sequences so they can prime amplification from the intermediate product produced from the internal primers. (The same universal sequences are typically employed from reaction to reaction; the first universal sequence can be the same as or different from the second universal sequence, as discussed in greater detail below.) Different pairs of forward and reverse external primers generally comprise different first and optional second tag sequences, such that an association is created between a particular first (and optional second) tag sequence and the source from which the external primers containing these tags were used to amplify the target region. The sequence of the first and optional second tag can therefore be used to uniquely identify the source for each amplified target region. The products from different amplification reactions can then be pooled for subsequent handling, for example, subsequent selective degradation of nucleic acids not produced by the forward and reverse external primers, ligation, exonuclease treatment, size-selection purification to remove primers from the tagged amplified products, nucleic acid sequencing, and/or the like. The number of different amplification reactions can be varied as desired for the particular application, e.g., 10 or more, 50 or more, 96 or more, 384 or more, or even 1536 or more.

It will be evident that, in embodiments in which the same target region is amplified from different sources, the precise polynucleotide sequence of the target region can differ from source to source. For example, the target region amplified from different individuals may contain different mutations, insertions, deletions, SNPs, markers, or the like. It will also be evident that the methods can be employed for amplification and tagging of different targets, from the same or different sources. Where different targets are to be amplified, different internal primer pairs including appropriate target-specific regions are employed in different reactions. The internal primers for different targets can include the same universal sequences if desired.

It will also be evident that any of a variety of tagging and pooling strategies can be employed, depending on the desired application. For example, where three different target regions are to be analyzed for each of multiple individuals, for each individual each target can be amplified and tagged using appropriate internal primers and external primers bearing a sequence tag to identify that individual (in either a two-step or a single step process); the resulting tagged products for all the targets and individuals can then be pooled. Alternatively, for each individual, each target can be amplified using appropriate internal primers, the three intermediate products from each individual can then be pooled for the second stage of amplification using external primers bearing a sequence tag for that individual, and the resulting tagged targets for all individuals can then be pooled. As yet another alternative, for each individual, all three targets can be amplified in a single reaction including three sets of internal primers and a set of external primers bearing a sequence tag for that individual; the resulting tagged targets for all individuals can then be pooled. Additional strategies will be immediately apparent to one of skill.

Figure 9:
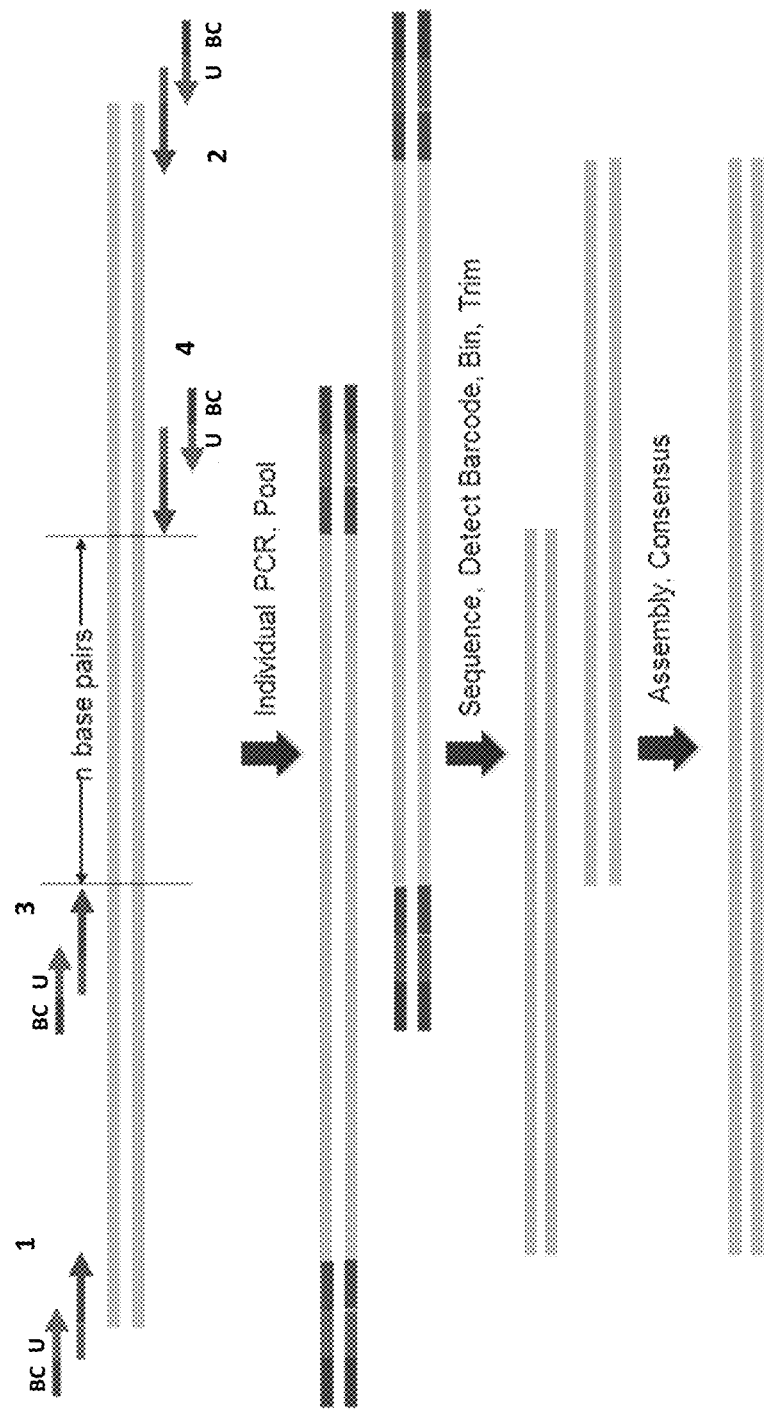
FIG. 9 schematically illustrates amplification and tagging of overlapping target regions, after which amplified products are pooled and sequenced and their sequences are assembled.

In another exemplary strategy, staggered sets of primers are employed to amplify overlapping target regions. Amplicons from a single sample source can be assigned a particular barcode, amplified separately, and then pooled, e.g., with each other and with similar amplicons amplified from different sources and tagged with different barcodes. As schematically illustrated in FIG. 9, a nucleic acid including multiple overlapping target regions is provided, as are staggered sets of internal and external primer pairs. Each internal primer includes a universal sequence (U) and a sequence complementary to part of the target region. Each external primer includes a universal sequence and a tag sequence (BC). Amplification is performed (in one or two steps, as desired) with suitable pairs of primers separately; for example, with primer sets 1 and 4 in one reaction and sets 2 and 3 in another reaction. Typically, the internal primers do not overlap the same region of the reverse complementing PCR primers, and a reasonable distance between the 3' ends of the PCR primers (relative to the aligned target template) is provided to allow for proper assembly during subsequent data processing and assembly steps. The resulting amplicons can then be pooled and their sequence determined. Once sequenced, an algorithmic mechanism can be employed to detect the barcode sequence of each resulting sequencing output, bin sequencing reads according the barcode identifier, trim the region that is the primer region, assemble, and generate a consensus sequence.

Various configurations for the tag sequences can be employed, as desired. For example, a single tag sequence can be added to one end of the target region. As another example, a single tag sequence can be added to both ends of the target region (e.g., both forward and reverse external primers can include the same tag sequence, or, more preferably, the forward external primer includes the tag sequence while the reverse external primer includes its reverse complement). As yet another example, one tag sequence can be added to one end of the target region and a different tag sequence to the other end of the target region. In such embodiments, the two different tags can be employed to encode an increased number of options for a single type of information (e.g., the combination of the two tags can uniquely identify the source of the sample from which the target was amplified), or the two tags can encode different types of information (e.g., one can indicate the sample source while the other encodes time of collection or another feature).

Tag sequences can be of essentially any convenient length. Typically, the minimum length is determined by the number of possibilities to be encoded (and whether a single tag or a combination of two tags is to be employed for such encoding). A tag sequence can be, e.g., 5-25 nucleotides in length, e.g., 7-20 nucleotides or 10-16 nucleotides.

Similarly, various configurations for the universal sequences can be employed, depending on the desired application. For example, in embodiments in which a single tag sequence is to be added to both ends of the target region, the first and second universal sequences can be the same. In embodiments in which different sequences are to be added to the two ends of the target region, the first and second universal sequences are preferably different. The universal sequences can be of essentially any convenient length that permits efficient synthesis, annealing and priming. For example, a universal sequence can be 7-50 nucleotides in length, e.g., 16-35 nucleotides or 18-30 nucleotides.

The target-specific sequences employed in the primers can be of essentially any convenient length that permits efficient synthesis, annealing, and priming. For example, a target-specific sequence can be 7-50 nucleotides in length, e.g., 16-35 nucleotides or 18-30 nucleotides.

Sequences employed in the primers (e.g., tag sequences, universal sequences, and target-specific sequences) are preferably designed to have minimal potential for intramolecular secondary structure formation or for cross-hybridization with each other, with undesired portions of the target region, and with other nucleic acids expected to be present during the amplification reaction. Principles for primer design are well known in the art and readily applied by one of skill. Such principles include considering the reaction temperature and the melting temperature of the primers (e.g., of the template-specific region of the primer), GC content, avoidance of long single polynucleotide runs or dinucleotide repeats, and the like.

The target region can be derived from essentially any desired source, e.g., genomic DNA, cloned DNA (e.g., BACs, YACs, PACs, etc.), RNA (e.g., mRNA, tRNA, rRNA, ribozymes, etc.), cDNA, or a combination thereof. The sample from which the target is derived can be a metagenomic sample, e.g., an environmental or intestinal sample. Nucleic acids can be collected from various sources including, but not limited to, whole blood, semen, saliva, tears, urine, fecal material, sweat, buccal cells, skin, and hair. The nucleic acids can be obtained from the same individual, which can be a human or other species (e.g., plant, bacteria, fungi, algae, archaea, etc.), or from different individuals of the same species, or different individuals of different species. Methods for generating a nucleic acid sample, e.g., from one of the sources listed above, are known and routine to those of ordinary skill in the art. Typically they involve cell lysis, stabilization and protection of the nucleic acids (e.g., from nuclease digestion), isolation of the nucleic acids from other components (e.g., proteins, carbohydrates, lipids, etc.) of the original sample, and optional fragmentation, e.g., by chemical, enzymatic, or mechanical means. A variety of commercial kits for purification of nucleic acids are available.

Exonuclease Trimming

In another aspect of the invention, exonuclease trimming by a polymerase is used to create 5' overhangs on a desired nucleic acid fragment, for example, an amplified, tagged target region. Ligation of stem-loop adapters specifically to the overhangs created protect the desired fragment, while any other nucleic acids present are selectively degraded.

Thus, one general class of embodiments provides methods of making a circular nucleic acid. In the methods, a target nucleic acid region is amplified to provide a double-stranded product. The product can have, e.g., blunt ends or 3'-overhangs (e.g., 3' A overhangs), depending on the particular polymerase employed in the amplification reaction. The double-stranded product is treated with an enzyme having polymerase activity and 3'→5' exonuclease activity, in the presence of at most three types of dNTPs, to produce a sticky-ended product having 5' overhangs. Typically, treatment is performed in the presence of at most two types of dNTPs, and preferably in the presence of a single type of dNTP. Exemplary enzymes having both polymerase and 3'→5' exonuclease activity are known in the art and are commercially available. Suitable enzymes include, but are not limited to, T4 DNA polymerase.

A first stem-loop adapter is ligated to one end of the sticky-ended product and a second stem-loop adapter is ligated to the other end of the sticky-ended product. It will be evident that the stem-loop adapters preferably each include a 5' overhang complementary to an overhang on the product. The resulting molecule is a circular nucleic acid having a double-stranded central region (comprising the target region and the stems of the adapters) and two single-stranded hairpin end regions (that is, loops connecting the two complementary strands of the double-stranded region, corresponding to the loops of the adapters). As will be appreciated, the term circular, when referring to the strand configuration, merely denotes a strand of a nucleic acid that includes no terminal nucleotides, and does not necessarily denote any geometric configuration. Production of such circular nucleic acids by ligation of stem-loop adapters is described, e.g., in U.S. Pat. No. 8,153,375 "Compositions and Methods for Nucleic Acid Sequencing" and in Travers et al. (2010) Nucl. Acids Res. 38(15):e159, each of which is incorporated herein by reference in its entirety for all purposes.

Any other nucleic acids present are then selectively degraded, for example, by exposure to one or more exonucleases (e.g., ExoIII and ExoVII). The one or more exonucleases selectively degrade any single-stranded or non-circular double-stranded nucleic acid present but do not degrade the circular nucleic acid, which has no free termini and therefore survives the exonuclease treatment intact. The exonuclease can then be deactivated (e.g., heat killed) or removed.

Figure 3:
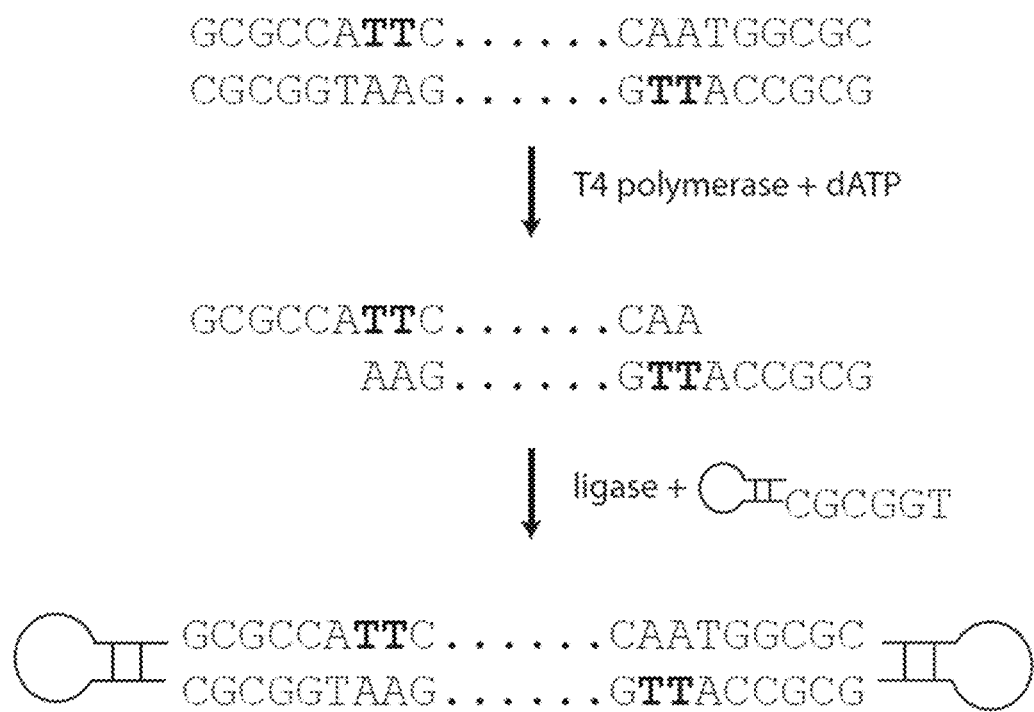
FIG. 3 schematically illustrates a method in which exonuclease trimming is employed to create sticky ends on a nucleic acid product.

An exemplary embodiment is schematically illustrated in FIG. 3. A double-stranded nucleic acid (e.g., a PCR product) is treated with T4 polymerase in the presence of a single nucleotide (dATP in this example). T4 polymerase's 3'→5' exonuclease activity digests a 3' end of the double-stranded DNA until it reaches a base on the opposite strand complementary to the dNTP present in solution (the stop base, T in this example). Since the polymerase activity of T4 polymerase incorporates an A at this position whenever the exonuclease activity removes an A, the exonuclease and polymerase activities become balanced at the stop base, and a 5' overhang is created. Factors such as incubation time (e.g., forty minutes) and dNTP concentration (e.g., 250 µM) can be varied to optimize overhang formation. A hairpin adapter having a complementary 5' overhang is then ligated to the overhang created at each end of the nucleic acid, producing a circular nucleic acid. Since the circular nucleic acid has no free termini, it is protected from subsequent exonuclease treatment.

More than one tandem stop base is optionally present. Having two, three, four, five, six, or even more tandem stop bases can help ensure that exonuclease digestion halts at the desired point, rather than creating a longer than desired overhang. Typically, regardless of the number of tandem stop bases, a single type of stop base is employed and a single type of dNTP is provided along with the T4 polymerase or similar enzyme, so that the other three bases can be employed in the resulting sticky end, maximizing the possible complexity of the resulting overhangs. As noted above, however, two or three different types of dNTPs can be provided, in which case two or three different types of stop base can be employed and only the other two or one bases are present in the overhangs.

In one class of embodiments, the two 5' overhangs in the sticky ended product have the same polynucleotide sequence, as in the exemplary embodiment illustrated in FIG. 3. A single type of stem-loop adapter with a complementary 5' overhang can thus ligate to both ends of the product. In another class of embodiments, the two 5' overhangs on the sticky-ended product have different polynucleotide sequences. In such embodiments, the first stem-loop adapter has a 5' overhang complementary to one of the overhangs on the product and the second stem-loop adapter has a 5' overhang complementary to the other overhang on the product. It will be evident that one end of the product could remain blunt (e.g., where the end terminates with the stop base) while the other end becomes sticky; a blunt ended stem-loop adapter could then be ligated to the blunt end of the product while a sticky ended adapter is ligated to the other. Having two sticky ends is generally preferable, however, for most efficient ligation.

The target nucleic acid region can be amplified by essentially any convenient technique, e.g., PCR. The primers employed for the amplification are preferably designed to produce overhangs of the desired sequence. Thus, in one class of embodiments, the target nucleic acid region is amplified using a forward primer comprising a first end sequence and at least one stop base and a reverse primer comprising a second end sequence and at least one stop base. It will be evident that the polynucleotide sequence of the end sequences determines the sequence of the resulting overhangs. Accordingly, the end sequence is located at the 5' end of the primer and is immediately followed by the stop base(s). No nucleotide in the first and second end sequences is complementary to any of the dNTPs present in the treating step, and each stop base is complementary to a dNTP present in the treating step.

The first and second end sequences can be identical, e.g., in embodiments in which the same type of stem-loop adapter is ligated to both ends of the resulting sticky-ended product. In other embodiments, the first and second end sequences comprise different polynucleotide sequences. The resulting 5' overhangs on the sticky ended product are thus different, and different stem-loop adapters can be conveniently ligated to the different ends.

In one class of embodiments, the target region is amplified in a single stage, using a single primer pair. The forward primer has a first end sequence followed by at least one stop base at its 5' end, and a first target-specific sequence at its 3' end. Similarly, the reverse primer has a second end sequence followed by at least one stop base at its 5' end, and a second target-specific sequence at its 3' end. The first and second target-specific sequences anneal to sites that flank the target region on opposite strands of the template containing the target region. One or both primers optionally include a tag sequence, typically between the stop base and the target-specific sequence. When both primers include a tag sequence, the tags can be the same or different.

In another class of embodiments, the target region is amplified in two stages, employing two pairs of primers (a pair of internal primers that add universal sequences to the target region in an intermediate product, and a pair of external primers). As for the embodiments described above, the two stages can be performed sequentially in separate reactions, or they can be performed in a single reaction. The forward internal primer comprises a first universal sequence and a first target-specific sequence, and the reverse internal primer comprises a second universal sequence and a second target-specific sequence. The first and second target-specific sequences anneal to sites that flank the target region on opposite strands of the template containing the target region. The target-specific sequences are preferably at the 3' end of the internal primers. The forward external primer has a first end sequence followed by at least one stop base at its 5' end, and the first universal sequence at its 3' end. The reverse external primer has a second end sequence followed by at least one stop base at its 5' end, and the second universal sequence at its 3' end. One or both external primers optionally include a tag sequence, typically between the stop base and the universal sequence. When both of the external primers include a tag sequence, the tags can be the same or different (e.g., both forward and reverse external primers can include the same tag sequence, or, more preferably, the forward external primer can include the tag sequence while the reverse external primer includes its reverse complement, or the two tag sequences can be independent of each other).

The first and second end sequences can be the same or different, independent of any tag sequences. For example, the first and second tag sequences can comprise different polynucleotide sequences, while the first and second end sequences comprise the same polynucleotide sequence (e.g., in embodiments in which the same type of stem-loop adapter, e.g., including a sequencing primer binding site, is to be ligated to both ends but two different tags are desired). As another example, the first and second tag sequences can comprise the same polynucleotide sequence (or a sequence and its reverse complement), while the first and second end sequences comprise different polynucleotide sequences (e.g., in embodiments in which different types of stem-loop adapters, e.g., one including a sequencing primer binding site and the other not, are to be employed but only a single type of tag is desired). As yet other examples, the first and second tag sequences can be the same and the first and second end sequences can be the same, or the first and second tag sequences can be different and the first and second end sequences can be different.

The end sequences, and thus the resulting 5' overhangs (and the complementary overhangs on the adapters), can be of essentially any convenient length. Typically, the end sequence or overhang is 3-20 nucleotides long, e.g., 4-12 nucleotides or 4-8 nucleotides.

It will be evident that the forward and reverse internal primers should not include the first or second end sequence at their 5' ends, to ensure that the intermediate product lacking the optional tags is not undesirably capable of forming sticky ends that can ligate to the stem-loop adapters. The internal primers optionally include at least one stop base at their 5' end, so the resulting intermediate product remains blunt ended during treatment with the T4 polymerase (or similar enzyme) and dNTP(s). As another option, the 5' end of an internal primer can include one or two bases not complementary to the dNTPs present in the treatment step followed by a stop base, so that only a one or two base overhang is created that is unlikely to mis-hybridize and ligate to the stem-loop adapter.

Primers (e.g., both primers in one stage embodiments and the external primers in two stage embodiments) and stem-loop adapters can be synthesized with a free 5' phosphate group as is known in the art. When primers and/or adapters lacking a 5' phosphate are employed, the sticky-ended product and/or the adapters can be phosphorylated by treatment with T4 polynucleotide kinase or similar enzyme as is well known in the art prior to the ligation step.

The methods are suitable for circularizing (and optionally tagging) large numbers of nucleic acids, for example, in highly multiplexed or high throughput applications. As just one example, the methods can be applied to amplification, optional tagging, and subsequent analysis of a given target from a number of different sources (e.g., a genomic region, cDNA, or the like from multiple individuals (e.g., humans), or a pathogen-identifying target or other species-identifying target from samples obtained from multiple different locations, individuals, or batches of food or other product). Targets obtained from different sources are amplified (and optionally tagged, e.g., to identify the source) in separate reactions. As another example, different targets can be amplified and optionally tagged (from the same source or different sources) in different reactions. In both examples, the resulting double-stranded amplification products are typically pooled before the step of treating with T4 polymerase or similar enzyme. Various tagging and/or pooling strategies can be employed, as detailed for the blocked primer embodiments above.

Essentially all of the features noted for the embodiments above apply to these embodiments as well, as relevant, for example, with respect to choice and configuration of target-specific sequences, universal sequences, and/or tag sequences, source of the target nucleic acid, primer ratios, primer design, multiplexing, pooling strategies, and/or the like.

It will be evident that techniques other than amplification as detailed above can be employed to provide the double-stranded nucleic acid containing the target region that is subjected to exonuclease trimming. For example, a nucleic acid sample that includes the target region (e.g., a sample of genomic DNA, a cDNA or other library, or essentially any nucleic acids) can be subjected to tagmentation with a transposase that fragments the sample and adds a known sequence to the ends of the fragments. Thus, in another general class of embodiments for making a circular nucleic acid, a nucleic acid sample comprising a target region is exposed to a transposase and to at least one adapter that comprises a transposon end sequence, under conditions wherein a transposition reaction is catalyzed by the transposase, to produce a double-stranded nucleic acid comprising the target region. The ends of the nucleic acid include the transposon end sequence. The double-stranded nucleic acid is treated with an enzyme having polymerase activity and 3'→5' exonuclease activity, in the presence of at most three types of dNTPs, to produce a sticky-ended product having 5' overhangs. As for the embodiments described above, treatment is typically performed in the presence of at most two types of dNTPs, and preferably in the presence of a single type of dNTP. Exemplary enzymes having both polymerase and 3'→5' exonuclease activity are known in the art and are commercially available. Suitable enzymes include, but are not limited to, T4 DNA polymerase.

A first stem-loop adapter is ligated to one end of the sticky-ended product and a second stem-loop adapter is ligated to the other end of the sticky-ended product. It will be evident that the stem-loop adapters preferably each include a 5' overhang complementary to an overhang on the product. The resulting molecule is a circular nucleic acid having a double-stranded central region (comprising the target region and the stems of the adapters) and two single-stranded hairpin end regions (that is, loops connecting the two complementary strands of the double-stranded region, corresponding to the loops of the adapters).

Any other nucleic acids present are then selectively degraded, for example, by exposure to one or more exonucleases (e.g., ExoIII and ExoVII). The one or more exonucleases selectively degrade any single-stranded or non-circular double-stranded nucleic acid present but do not degrade the circular nucleic acid, which has no free termini and therefore survives the exonuclease treatment intact. The exonuclease can then be deactivated (e.g., heat killed) or removed.

Suitable transposases, including hyperactive transposases (e.g., hyperactive variants of Tn5 transposase), are known in the art. Transposon end sequences (the nucleotide sequences that are required for a double-stranded oligonucleotide or other nucleic acid to form a complex with the transposase that is functional in a transposition reaction) for use with such transposases are likewise known in the art, as are suitable reaction conditions. See, e.g., U.S. Pat. No. 9,080, 211, Adey et al. (2010) "Rapid, low-input, low-bias construction of shotgun fragment libraries by high-density in vitro transposition" Genome Biol. 11(12):R119, Adey and Shendure (2012) "Ultra-low-input, tagmentation-based whole-genome bisulfite sequencing" Genome Res. 22(6): 1139-43, and Picelli et al. (2014) "Tn5 transposase and tagmentation procedures for massively scaled sequencing projects" Genome Res. 24: 2033-2040, each of which is hereby incorporated by reference in its entirety for all purposes.

Double-stranded adapters including the transposon end can readily be synthesized using well known techniques. The transposon end sequence itself (or a portion thereof) can be employed as the end sequence and stop base detailed above, or in addition to the transposon end sequence an end sequence and stop base can be included in the adapter (e.g., 5' of the transferred strand sequence; for an exemplary transferred strand sequence, see, e.g., U.S. Pat. No. 9,080, 211). A single type of adapter can be employed such that resulting fragments have an identical sequence transferred to both ends, or two different adapters (e.g., bearing different end sequences 5' of a stop base and the transferred strand sequence of the transposon end sequence) can be employed, such that some of the resulting fragments have a different sequence transferred to each of the two ends.

The product of tagmentation can be treated with the enzyme having polymerase activity and 3'→5' exonuclease activity, in the presence of at most three types of dNTPs, immediately after its formation. In other embodiments, 5' overhangs left on the tagmentation products by action of the transposase can be filled in to produce a blunt ended double-stranded product, e.g., with T4 polymerase, a strand-displacing polymerase such as Φ29, or another suitable polymerase and a mixture of nucleotides (which are then removed), prior to treatment with the enzyme having polymerase activity and 3'→5' exonuclease activity in the presence of at most three types of dNTPs. In other embodiments, a short gap left on one strand at each end of the tagmentation products by action of the transposase can be filled, e.g., by a polymerase and nucleotide mixture or a complementary oligonucleotide and a ligase prior to treatment with the enzyme having polymerase activity and 3'→5' exonuclease activity.

In one class of embodiments, the two 5' overhangs on the sticky ended product have the same polynucleotide sequence; a single type of stem-loop adapter with a complementary 5' overhang can thus ligate to both ends of the product. In another class of embodiments, the two 5' overhangs on the sticky-ended product have different polynucleotide sequences. In such embodiments, the first stem-loop adapter has a 5' overhang complementary to one of the overhangs on the product and the second stem-loop adapter has a 5' overhang complementary to the other overhang on the product. In another class of embodiments, the two 5' overhangs on the sticky ended product have the same polynucleotide sequence, and two different types of stem-loop adapter with a complementary 5' overhang are employed; the desired asymmetric product (having two different adapters rather than two copies of one of the adapters) is optionally selected, e.g., by hybridization to an immobilized oligonucleotide complementary to one of the loops to select products having one type of adapter followed by hybridization to a different oligonucleotide complementary to the other loop to select products also having the other type of adapter. The selected asymmetric product is optionally then sequenced, e.g., using a primer complementary to one of the loops. In other embodiments, hybridization to an immobilized oligonucleotide complementary to one of the loops can select products having one type of adapter, and sequencing can then be performed using a primer complementary to the other type of adapter; products lacking the second adapter will not provide sequence information.

It will be evident that one end of the product could remain blunt (e.g., where the end terminates with the stop base) while the other end becomes sticky; a blunt ended stem-loop adapter could then be ligated to the blunt end of the product while a sticky ended adapter is ligated to the other. Having two sticky ends is generally preferable, however, for most efficient ligation.

Essentially all of the features noted for the embodiments above apply to these embodiments as well, as relevant, for example, with respect to use of tandem stop bases, configuration of stem-loop adapters, presence of tag sequence(s), configuration of end sequences and resulting overhangs, source of the target nucleic acid, multiplexing, pooling strategies, and/or the like.

As another example, the double-stranded nucleic acid containing the target region that is subjected to exonuclease trimming can be provided by ligation of oligonucleotide adapters. Thus, in yet another general class of embodiments for making a circular nucleic acid, a nucleic acid sample (e.g., a sample of genomic DNA, a cDNA or other library, or essentially any nucleic acids) comprising a target region is provided. If the nucleic acids in the sample are not already blunt ended and/or 5' phosphorylated, end repair can be performed. A blunt ended, double-stranded oligonucleotide adapter is provided. The first strand of the adapter includes the end sequence and at least one stop base. The 5' end of the first strand can include a free 5' hydroxyl group or a removable blocking group (e.g., a chemically removable blocking group, a site for a nicking endonuclease between a 5' blocking group such as a 5' amino modifier and the end sequence such that the nick would release the blocking group, or the like); the 5' end can but preferably does not include a free phosphate group. The 3' end of the first strand includes a free 3' hydroxyl group. The second strand of the adapter includes a free 5' phosphate group but does not include a free 3' hydroxyl group. For example, the second strand can include a blocked 3' hydroxyl group or a 3' terminal dideoxy nucleotide. Since the adapter has free 3' hydroxyl and 5' phosphate groups at one of its ends, it can be ligated to a nucleic acid in the sample. The absence of a free 3' hydroxyl (and preferably of a free 5' phosphate) on the other end, however, prevents ligation of that end to another nucleic acid in the sample or to another adapter. The blocking group therefore permits addition of a single adapter to each end of each nucleic acid molecule in the sample. When a 5' hydroxyl is provided on the first strand of the adapter, a phosphate group is added prior to ligation. Similarly, when a 5' blocking group is provided on the first strand of the adapter, the blocking group is removed prior to ligation.

Following ligation, the resulting double-stranded nucleic acid is treated with an enzyme having polymerase activity and 3'→5' exonuclease activity, in the presence of at most three types of dNTPs, to produce a sticky-ended product having 5' overhangs. As for the embodiments described above, treatment is typically performed in the presence of at most two types of dNTPs, and preferably in the presence of a single type of dNTP. Exemplary enzymes having both polymerase and 3'→5' exonuclease activity are known in the art and are commercially available. Suitable enzymes include, but are not limited to, T4 DNA polymerase.

A first stem-loop adapter is ligated to one end of the sticky-ended product and a second stem-loop adapter is ligated to the other end of the sticky-ended product. It will be evident that the stem-loop adapters preferably each include a 5' overhang complementary to an overhang on the product. The resulting molecule is a circular nucleic acid having a double-stranded central region (comprising the target region and the stems of the adapters) and two single-stranded hairpin end regions (that is, loops connecting the two complementary strands of the double-stranded region, corresponding to the loops of the adapters).

Any other nucleic acids present are then selectively degraded, for example, by exposure to one or more exonucleases (e.g., ExoIII and ExoVII). The one or more exonucleases selectively degrade any single-stranded or non-circular double-stranded nucleic acid present but do not degrade the circular nucleic acid, which has no free termini and therefore survives the exonuclease treatment intact. The exonuclease can then be deactivated (e.g., heat killed) or removed.

It will be evident that one end of the product could remain blunt (e.g., where the end terminates with the stop base) while the other end becomes sticky; a blunt ended stem-loop adapter could then be ligated to the blunt end of the product while a sticky ended adapter is ligated to the other. Having two sticky ends is generally preferable, however, for most efficient ligation.

Essentially all of the features noted for the embodiments above apply to these embodiments as well, as relevant, for example, with respect to use of tandem stop bases, configuration of stem-loop adapters, presence of tag sequence(s), configuration of end sequences and resulting overhangs, source of the target nucleic acid, multiplexing, pooling strategies, assembly, and/or the like.

The circular nucleic acid product resulting from the methods described herein can be employed in essentially any desired application, e.g., nucleic acid sequencing, amplification, analysis, or the like. As just one example, tagged circular nucleic acid products produced from genomic DNA fragments from each of two or more individuals (where the tag(s) indicate the source of the sample) can be pooled and sequenced. In such embodiments, it will be evident that the target region can refer to any region whose sequence is to be determined; a target region can but need not be a predetermined, specific region, locus, or the like. Where multiple target regions, e.g., multiple genomic DNA fragments from an individual, are tagged and sequenced, after sequence data is obtained an algorithmic mechanism can be employed to detect the barcode tag sequence of each resulting sequencing output, bin sequencing reads according the barcode identifier, trim the regions to remove adapter or primer sequences or the like, assemble, and generate a consensus sequence. If desired, the circular nucleic acid can be fully or partially linearized, e.g., by digestion with a restriction enzyme that recognizes a site in the stem of the adapter(s). Optionally, in embodiments in which two different adapters are employed, one adapter includes the restriction enzyme recognition site and the other does not, such that digestion produces a long hairpin, optionally including a 5' overhang. As another example, in embodiments in which the two end sequences (and thus the resulting 5' overhangs) are different, a single stem-loop adapter complementary to only one of the overhangs can be employed during the ligation step, while a 5' overhang is left on the other end, producing a long hairpin.

Nucleic Acid Sequencing

The methods are particularly suitable for amplifying, optionally tagging, and circularizing target regions for subsequent determination of their polynucleotide sequence. Any of the methods described herein can thus also include determining a polynucleotide sequence of the target region, and also of any tag sequence(s) added to the target region. In embodiments in which multiple target regions are amplified, e.g., in separate reactions and pooled, the methods can include determining the polynucleotide sequence of multiple target regions. The methods optionally also include using the tag sequence(s) so determined to identify the source of the target region (or to provide other information about the target region that was encoded by the tag or tags).

Sequencing can be performed by essentially any desired technique. For example, the PACBIO SEQUEL or RS II SMRT® DNA sequencing system commercially available from Pacific Biosciences of California, Inc. (www dot pacificbiosciences dot com) can be employed for its long read length, obtained through real time, single molecule sequencing in zero mode waveguides. See, e.g., U.S. Pat. Nos. 7,056,661, 7,052,847, 7,033,764, 7,056,676, and 8,153,375, the full disclosures of which are incorporated herein by reference in their entirety for all purposes, for discussion of this sequencing technique. Preferred templates for use with the SMRT® system are circular nucleic acids having a double-stranded central region and two single-stranded hairpin end regions (SMRTBELLs), such as the circular nucleic acids produced by the methods of the invention. At least one of the end regions (and optionally both) typically includes a binding site for a sequencing primer.

Molecular Biological Techniques

Additional details on synthesis, isolation, amplification, hybridization, and manipulation of nucleic acids (e.g., to produce primers, adapters, templates, and the like or for subsequent manipulation of progeny nucleic acids) are available in the art. These techniques are well known and are explained in, for example, Basu (Ed.) (2015) PCR Primer Design—Methods in Molecular Biology, Humana Press; van Pelt-Verkuil et al. (2010) Principles and Technical Aspects of PCR Amplification, Springer; Innis et al. (Eds.) (1990) PCR Protocols A Guide to Methods and Applications, Academic Press Inc., San Diego; Innis et al. (Eds.) (1995) PCR Strategies, Academic Press Inc., San Diego; Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; Kaufman et al. (2003) Handbook of Molecular and Cellular Methods in Biology and Medicine Second Edition Ceske (ed) CRC Press; Tijssen (1993) Laboratory Techniques in Biochemistry and Molecular Biology—Hybridization with Nucleic Acid Probes part I chapter 2, "Overview of principles of hybridization and the strategy of nucleic acid probe assays," (Elsevier, New York); and Current Protocols in Molecular Biology, F. M. Ausubel et al., eds., Current Protocols, a joint venture between Greene Publishing Associates, Inc. and John Wiley & Sons, Inc., (supplemented through 2015). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York); and Atlas and Parks (Eds.) The Handbook of Microbiological Media (1993) CRC Press, Boca Raton, Fla.

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references. In addition, essentially any polynucleotide (including, e.g., 5' phosphorylated or 5' blocked polynucleotides) can be custom or standard ordered from any of a variety of commercial sources, such as Integrated DNA Technologies (www (dot) idtdna (dot) com), The Midland Certified Reagent Company (www (dot) mcrc (dot) com), The Great American Gene Company (www (dot) genco (dot) com), ExpressGen Inc. (www (dot) expressgen (dot) Qiagen (oligos (dot) qiagen (dot) coin), and many others. Oligonucleotides intended for use as stem-loop adapters can be denatured and then intramolecularly annealed to achieve the desired secondary structure prior to use.

Compositions, Systems, and Kits

Compositions, kits, and systems related to, produced by, or of use in the methods are another feature of the invention.

For example, one general class of embodiments provides a composition that includes a nucleic acid comprising a target region, a forward internal primer comprising a first universal sequence and a first target-specific sequence, a reverse internal primer comprising a second universal sequence and a second target-specific sequence, a forward external primer comprising the first universal sequence and a first tag sequence, and a reverse external primer comprising the second universal sequence and an optional second tag sequence, wherein the first and second target-specific sequences anneal to sites in the nucleic acid that flank the target region on opposite strands. The composition optionally includes a polymerase, one or more nucleotides and/or nucleotide analogs, buffer, salts, metal ions, and the like as known in the art, for example, as appropriate for an amplification reaction.

In one class of embodiments, the forward and reverse internal primers are 5' blocked. In another class of embodiments, the forward and reverse internal primers lack a free 5' phosphate group, and the forward and reverse external primers comprise a free 5' phosphate group.

Essentially all of the features noted for the methods above apply to the composition embodiments as well, as relevant; for example, with respect to choice and configuration of target-specific sequences, universal sequences, and/or tag sequences, source of the target nucleic acid, primer ratios, primer design, and/or the like.

Another general class of embodiments provides a composition that includes a circular nucleic acid comprising a double-stranded central region (including a first tag sequence, a first universal sequence, a target sequence, a second universal sequence, and an optional second tag sequence) and two single-stranded hairpin end regions; a nucleic acid comprising a double-stranded region having a 5' blocked terminus (and including the first universal sequence, the target sequence, the second universal sequence, and either the first or second tag sequence) and a single hairpin end region; and a double-stranded nucleic acid comprising the first universal sequence, the target sequence, and the second universal sequence, and having two 5' blocked termini. Optionally, the composition includes one or more exonucleases. Essentially all of the features noted for the methods above apply to the composition embodiments as well, as relevant.

The present invention also features kits that facilitate performance of the methods of the invention. For example, the kit can include useful reagents such as a polymerase, pairs of target-specific 5' blocked internal primers, pairs of external primers with different pairs bearing different tag sequences from other pairs but including the same universal sequences as the internal primers, one or more exonuclease (e.g., ExoIII and/or ExoVII), one or more stem-loop adapters, a ligase, and/or the like. As another example, the kit can include useful reagents such as a primer with a 5' end sequence followed by a stop base, an enzyme having polymerase activity and 3'→5' exonuclease activity, one or more stem-loop adapters, one or more exonuclease (e.g., ExoIII and/or ExoVII), a ligase, and/or the like. Depending upon the desired application, the kits of the invention optionally include additional reagents, such as one or more nucleotides or nucleotide analogs, a control template, a sequencing primer, and other reagents, such as buffer solutions and/or salt solutions, including, e.g., divalent metal ions. Such kits also typically include instructions for use of the compounds and other reagents in accordance with the desired application methods, e.g., nucleic acid amplification, sequencing, and the like.

In one aspect, the invention includes systems, e.g., systems used to practice the methods herein and/or comprising the compositions described herein, optionally in high-throughput mode. The system can include, e.g., a fluid handling element, a fluid containing element, a heat source and/or heat sink for achieving and maintaining a desired reaction temperature, and/or a robotic element that moves other components of the system from place to place as needed (e.g., a multiwell plate handling element).

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or heating and cooling elements). The computer can also receive data from other components of the system, e.g., from a detector, and can interpret the data, provide it to a user in a human readable format, or use that data to initiate further operations, in accordance with any programming by the user.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1: Ligation Efficiency of Amplicons Containing 5' Modified PCR Primers to Adapter Hairpins in the Presence of T4 DNA Ligase, T4 DNA Polymerase, and T4 Polynucleotide Kinase Primer Design Primers are designed to amplify from known target sequences. Primers are designed to be homologous to the target at the 3' end of each primer, with a different universal sequence at the 5' end of each primer in a pair. Each PCR reaction includes a total of two primers (one forward primer, one reverse primer). Pairs of PCR primers are synthesized containing: (1) no 5' modification; (2) a 5' phosphate group; or (3) a 5' NH4-C6 (amino C6) modification.

PCR Amplification

Targets are amplified with Qiagen LongRange polymerase, according to the manufacturer's recommendations. The reaction conditions are as follows: 93° C. for 3 minutes, followed by 30 cycles of the following: 93° C. for 15 seconds, 58° C. for 30 seconds, 68° C. for 2 minutes. Subsequently, a final incubation occurs at 68° C. for 7 minutes, and 4° C. for indefinitely. The resulting amplicons are AMPURE SPRI bead purified.

End Repair and Ligation

Purified amplicons are coincubated in the presence of T4 DNA Polymerase, T4 Polynucleotide Kinase, and T4 DNA Ligase. Additional reagent components include ATP, C2 blunt ended hairpin adapters, and Reaction Buffer (Buffer 2, New England Biosciences, Inc.). The reaction incubation conditions are as follows: 37° C. for 20 minutes, 25° C. for 15 minutes, 65° C. for 10 minutes, 4° C. for indefinitely. Upon completion of incubation, the reactions are AMPURE SPRI bead purified.

DNA Damage Repair

Samples are treated with Pacific Biosciences of California, Inc. Template Prep Buffer, NAD+, ATP High, dNTP, and DNA Damage Repair mix. The reaction incubation conditions are as follows: 37° C. for 20 minutes, 4° C. for indefinitely.

Exo Treatment

Repaired Template Mix is treated with ExoIII and ExoVII. The reaction incubation conditions are as follows: 37° C. for 60 minutes, 4° C. for indefinitely. Upon completion of incubation, the reactions are AMPURE SPRI bead purified. The resultant purified product is assessed for DNA yield via NanoDrop quantitation.

Results

The amplicons contain a 3' A base overhang, introduced during PCR. Treatment with T4 DNA polymerase generates blunt ends on the amplicons. Efficiency of ligation of the blunt ended amplicons to blunt ended hairpin adapters is assessed by quantitating the amount of DNA to survive treatment with exonuclease.

Figure 4:
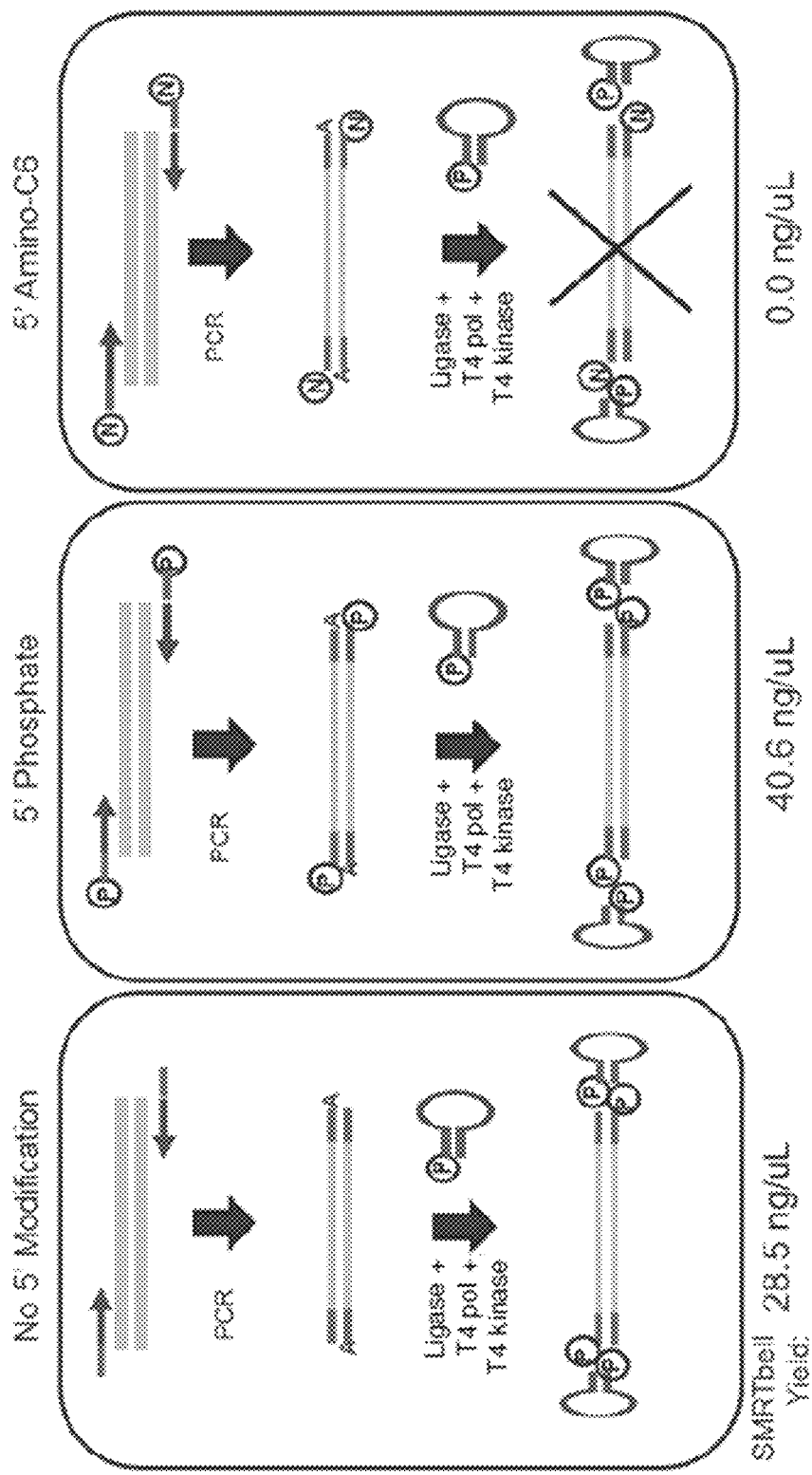
FIG. 4 schematically illustrates how 5' blocking of PCR primers produces amplicons that are not able to ligate to stem-loop adapters.

As shown in FIG. 4, in the presence of ATP and T4 DNA ligase, amplicons that contain a 5' phosphate group can be ligated to adapters to form stable SMRTBELL structures (circular nucleic acids with a double-stranded central region and two hairpin ends). The SMRTBELL circular nucleic acid templates are protected from exonuclease activity and are not degraded. Similarly, amplicons that contain an unmodified 5' end can also successfully generate stable, exonuclease-resistant SMRTBELL circular nucleic acid template structures in the presence of T4 polynucleotide kinase, ATP, and T4 DNA ligase. In contrast, amplicons that contain a 5' amino modification cannot ligate with the blunt end hairpin adapters and consequently do not form a structure that is protected from degradation upon exonuclease treatment. The results thus demonstrate that blocking the 5' end of the PCR primers effectively prevents ligation of the resulting 5' blocked amplicons.

Example 2: Favoring Amplicons Containing Barcoded Universal Primers in a Four Primer, Single PCR Primer Design Primers are designed to amplify from known target sequences. "Internal" primers are designed to be homologous to the target at the 3' end of each primer, with a different universal sequence at the 5' end of each primer in a pair. Each PCR reaction contains a total of two internal primers (one forward primer, one reverse primer). Pairs of internal PCR primers are synthesized containing: (1) no 5' modification; (2) a 5' phosphate group; or (3) a 5' NH4-C6 modification.

"External" primers are also designed, containing a universal sequence at the 3' end that is identical to the universal sequence contained in the corresponding internal primer (i.e., forward or reverse), along with a 16 bp unique barcode sequence at the 5' end of the primer. Each PCR reaction contains a total of two external primers (one forward primer, one reverse primer). Pairs of external PCR primers are synthesized containing: (1) no 5' modification; or (2) a 5' phosphate group.

PCR Amplification

Targets are amplified with Qiagen LongRange polymerase, according to the manufacturer's recommendations. Each reaction contains a plasmid containing a specific DNA target, along with the corresponding two internal primers and two external primers (i.e. four primers in a single PCR). The reaction conditions are as follows: 93° C. for 3 minutes, followed by 30 cycles of the following: 93° C. for 15 seconds, 54° C. for 30 seconds, 68° C. for 2 minutes. Subsequently, a final incubation occurs at 68° C. for 7 minutes, and 4° C. for indefinitely. The resulting amplicons are AMPURE SPRI bead purified.

End Repair and Ligation

Purified amplicons are coincubated in the presence of T4 DNA Polymerase, T4 Polynucleotide Kinase, and T4 DNA Ligase. Additional reagent components include ATP, C2 blunt ended hairpin adapters, and Reaction Buffer (Buffer 2, New England Biosciences, Inc.). The reaction incubation conditions are as follows: 37° C. for 20 minutes, 25° C. for 15 minutes, 65° C. for 10 minutes, 4° C. for indefinitely. Upon completion of incubation, the reactions are AMPURE SPRI bead purified.

DNA Damage Repair

Samples are treated with Pacific Biosciences of California, Inc. Template Prep Buffer, NAD+, ATP High, dNTP, and DNA Damage Repair mix. The reaction incubation conditions are as follows: 37° C. for 20 minutes, 4° C. for indefinitely.

Exo Treatment

Repaired Template Mix is treated with ExoIII and ExoVII. The reaction incubation conditions are as follows: 37° C. for 60 minutes, 4° C. for indefinitely. Upon completion of incubation, the reactions are AMPURE SPRI bead purified. The resultant purified SMRTBELL circular nucleic acid template product is assessed for DNA yield via NanoDrop quantitation.

Primer Annealing

The resulting SMRTBELL circular nucleic acid templates are annealed to C2v2 Primer (complementary to C2 adapter sequence, Pacific Biosciences of California, Inc.) in Sequencing Primer Buffer.

iTube Formation and Sequencing

Annealed templates are complexed with P6 enzyme (Pacific Biosciences of California, Inc.) according to the manufacturer's recommendations and run on the PacBio® RS II SMRT® DNA sequencing system with magbead loading and C4 chemistry. Bioinformatic analysis evaluates the ability to detect zero, one, or two barcodes within a SMRTBELL circular nucleic acid template structure (along with identifying the proportion of SMRTBELL circular nucleic acid templates in which barcode detection is indeterminant) for the six conditions listed in FIG. 5.

Results

Figure 5:
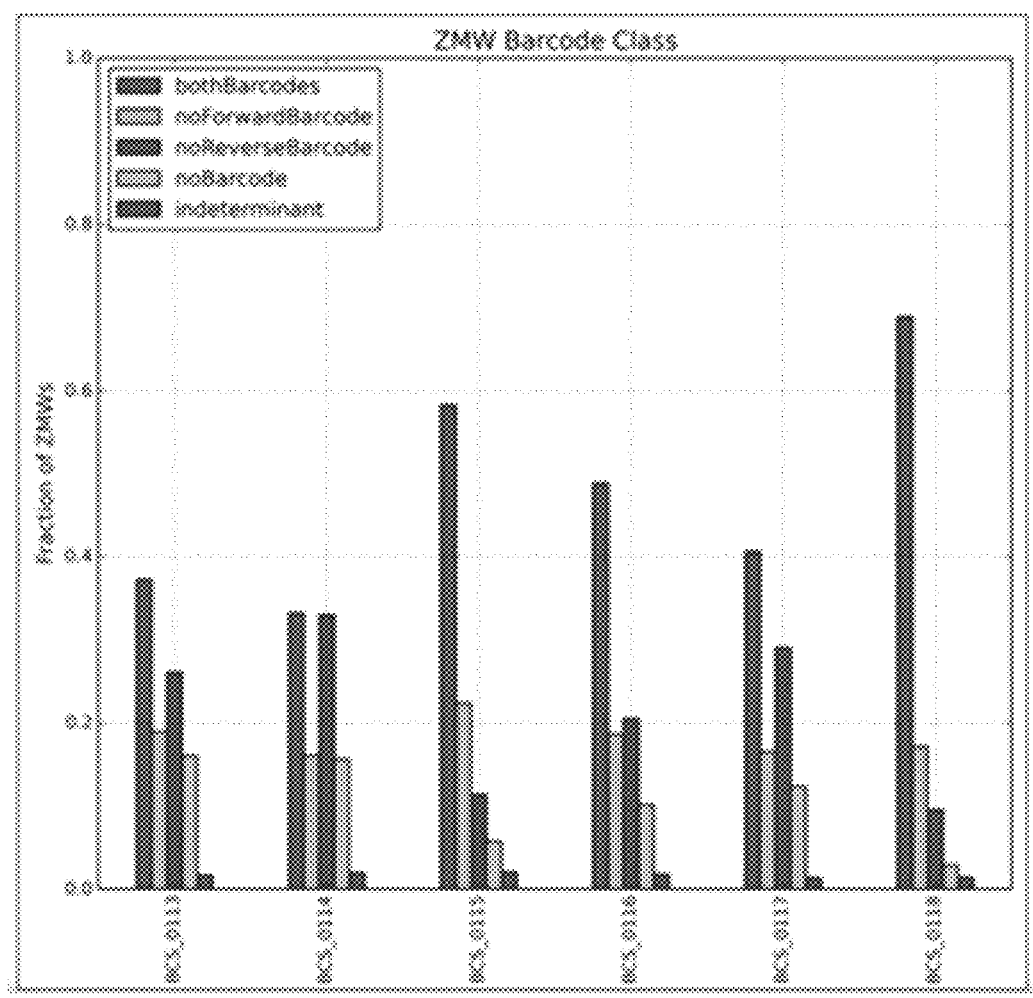
FIG. 5 shows a bar graph depicting the relative fraction of SMRTBELL circular nucleic acid template products having a barcode at both ends, having only a reverse barcode, having only a forward barcode, having no barcode, and having indeterminant barcodes, for SMRTBELL circular nucleic acid templates produced using the indicated combinations of modified and unmodified internal and external primers.

Bioinformatic analysis indicates that a higher proportion of the sequenced SMRTBELL circular nucleic acid templates contain a barcode on each end of the target (relative to one barcode on either side, no barcode on either side, or indeterminant barcode sequences on either side) when the internal primers contain the 5' NH4-C6 modification, as shown in FIG. 5. Blocking the 5' end of the internal primers thus favors production of amplicons with a barcode at both ends.

Example 3: Barcode Universal Amplification Utilizing Two Rounds of PCR, Each with Two Primers Primer Design Primers are designed to amplify from known target sequences. Internal primers are designed to be homologous to the target at the 3' end of each primer, with a different universal sequence at the 5' end of each primer in a pair. Pairs of internal PCR primers (one forward primer, one reverse primer) are synthesized containing a 5' NH4-C6 modification. External primers are also designed, containing a universal sequence at the 3' end that is identical to the universal sequence contained in the corresponding (i.e., forward or reverse) internal primer, along with a 16 bp unique barcode sequence at the 5' end of the primer. Pairs of external PCR primers (one forward primer, one reverse primer) are synthesized containing a 5' phosphate group.

PCR Amplification

Targets are amplified with Thermo Fisher HF polymerase, according to the manufacturer's recommendations.

Round 1 PCR:

Employs only the internal primers. The reaction is amplified using a plasmid containing a unique DNA target, in addition to a DNA spike of human genomic DNA (to serve as a surrogate for amplifying a DNA target from a complex DNA source in roughly the equivalent relative copy number). Ninety-six plasmids, each containing unique target sequences that are differentiated from each other from one to upwards of 14 single-nucleotide polymorphisms (SNPs), are used for amplification (in separate reactions). The reaction conditions are as follows: 98° C. for 30 seconds, followed by 20 cycles of the following: 98° C. for 10 seconds, 62° C. for 30 seconds, 72° C. for 1 minute. Subsequently, a final incubation occurs at 72° C. for 7 minutes, and 4° C. for indefinitely. The resulting amplicons are purified with Qiagen QIAQUICK spin column purification, followed by AMPURE SPRI bead purification and normalization of each of the ninety-six amplicons, based upon NanoDrop quantitation.

Round 2 PCR:

Employs only the external primers, along with an aliquot of round 1 amplicon. The reaction conditions are as follows: 98° C. for 30 seconds, followed by 20 cycles of the following: 98° C. for 10 seconds, 62° C. for 30 seconds, 72° C. for 1 minute. Subsequently, a final incubation occurs at 72° C. for 7 minutes, and 4° C. for indefinitely.

The ninety-six amplicons are pooled together into a single reaction (by transferring an equal volume from each), and the resulting pooled amplicons are purified with AMPURE SPRI bead purification and quantitated via NanoDrop.

End Repair and Ligation

Purified amplicons are coincubated in the presence of T4 DNA Polymerase, T4 Polynucleotide Kinase, and T4 DNA Ligase. Additional reagent components include ATP, C2 blunt ended hairpin adapters, and Reaction Buffer (Buffer 2, New England Biosciences, Inc.). The reaction incubation conditions are as follows: 37° C. for 20 minutes, 25° C. for 15 minutes, 65° C. for 10 minutes, 4° C. for indefinitely. Upon completion of incubation, the reaction is AMPURE SPRI bead purified.

DNA Damage Repair

Samples are treated with Pacific Biosciences of California, Inc. Template Prep Buffer, NAD+, ATP High, dNTP, and DNA Damage Repair mix. The reaction incubation conditions are as follows: 37° C. for 20 minutes, 4° C. for indefinitely.

Exo Treatment

Repaired Template Mix is treated with ExoIII and ExoVII. The reaction incubation conditions are as follows: 37° C. for 60 minutes, 4° C. for indefinitely. Upon completion of incubation, the reactions are AMPURE SPRI bead purified. The resultant purified product is assessed for DNA yield via NanoDrop quantitation.

Primer Annealing

SMRTbell™ templates are annealed to C2v2 Primer (complementary to C2 adapter sequence, Pacific Biosciences of California, Inc.) in Sequencing Primer Buffer.

iTube Formation and Sequencing

Annealed templates are complexed with P6 enzyme (Pacific Biosciences of California, Inc.) according to the manufacturer's recommendations and run on the PacBio® RS II SMRT® DNA sequencing system with magbead loading and C4 chemistry. Data is processed through SMRT® Portal data analysis workflow, which includes Long Amplicon Barcode analysis of the subsequent barcoded, binned, consensus sequences aligned to a list of reference sequences via BLASR alignment.

Results

Ninety-six targets are successfully amplified in two rounds of PCR (each using two primers), with each DNA target assigned a unique 16 bp tag sequence. Subsequent pooling of the amplicons and production of a single SMRT-BELL circular nucleic acid template preparation results in assignment of the resulting sequences to be binned according to the barcodes. Consensus alignments produced 100% sequence concordance relative to the corresponding reference sequences.

Example 4: Barcode Universal Amplification Utilizing One Round of PCR, with Four Primers Primer Design Primers are designed to amplify from known target sequences. Internal primers are designed to be homologous to the target at the 3' end of each primer, with a different universal sequence at the 5' end of each primer in a pair. Pairs of internal PCR primers (one forward primer, one reverse primer) are synthesized containing a 5' NH4-C6 modification. External primers are also designed, containing a universal sequence at the 3' end that is identical to the universal sequence contained in the corresponding (i.e., forward or reverse) internal primer, along with a 16 bp unique barcode sequence at the 5' end of the primer. Pairs of external PCR primers (one forward primer, one reverse primer) are synthesized containing a 5' phosphate group.

PCR Amplification

Targets are amplified with Thermo Fisher HF polymerase, according to the manufacturer's recommendations. The reaction is amplified using a plasmid containing a unique DNA target. Three hundred eighty-four plasmids, each containing unique target sequences that are differentiated from each other from one to upwards of 14 single-nucleotide polymorphisms (SNPs) are used for amplification (in separate reactions).

PCR:

The reaction conditions are as follows: 98° C. for 30 seconds, followed by 30 cycles of the following: 98° C. for 10 seconds, 64° C. for 30 seconds, 72° C. for 1 minute. Subsequently, a final incubation occurs at 72° C. for 7 minutes, and 4° C. for indefinitely. The resulting amplicons are purified with Qiagen QIAQUICK spin column purification, followed by AMPURE SPRI bead purification and normalization of each of the three hundred eighty-four amplicons, based upon NanoDrop quantitation.

The three hundred eighty-four amplicons (an equal volume of each) are pooled together into a single reaction volume, and the resulting pooled amplicons are purified with AMPURE SPRI bead purification and quantitated via Nano-Drop.

End Repair and Ligation

Purified amplicons are coincubated in the presence of T4 DNA Polymerase, T4 Polynucleotide Kinase, and T4 DNA Ligase. Additional reagent components include ATP, C2 blunt ended hairpin adapters, and Reaction Buffer (Buffer 2, New England Biosciences, Inc.). The reaction incubation conditions are as follows: 37° C. for 20 minutes, 25° C. for 15 minutes, 65° C. for 10 minutes, 4° C. for indefinitely. Upon completion of incubation, the reactions are AMPURE SPRI bead purified.

DNA Damage Repair

Samples are treated with Pacific Biosciences of California, Inc. Template Prep Buffer, NAD+, ATP High, dNTP, and DNA Damage Repair mix. The reaction incubation conditions are as follows: 37° C. for 20 minutes, 4° C. for indefinitely.

Exo Treatment

Repaired Template Mix is treated with ExoIII and ExoVII. The reaction incubation conditions are as follows: 37° C. for 60 minutes, 4° C. for indefinitely. Upon completion of incubation, the reactions are AMPURE SPRI bead purified. The resultant purified product is assessed for DNA yield via NanoDrop quantitation.

Primer Annealing

SMRTBELL circular nucleic acid templates are annealed to C2v2 Primer (complementary to C2 adapter sequence, Pacific Biosciences of California, Inc.) in Sequencing Primer Buffer.

iTube Formation and Sequencing

Annealed templates are complexed with P6 enzyme (Pacific Biosciences of California, Inc.) according to the manufacturer's recommendations and run on the PacBio® RS II SMRT® DNA sequencing system with magbead loading and C4 chemistry. Data is processed through SMRT® Portal data analysis workflow, which includes Long Amplicon Barcode analysis of the subsequent barcoded, binned, consensus sequences aligned to a list of reference sequences via BLASR alignment.

Results

Three hundred eighty-four targets are successfully amplified, each in a single round of PCR using four primers, with each DNA target assigned a unique 16 bp tag sequence. Subsequent pooling of the amplicons and production of a single SMRTBELL circular nucleic acid template preparation resulted in assignment of the resulting sequences to be binned according to the barcodes. The consensus alignments produced 100% sequence concordance relative to the corresponding reference sequences.

Example 5: T4 Peel Back

Primer Design

Primers are designed to amplify from a known vector. Primers are designed to be homologous to the target in all bases except for 8 bases at the 5' end of each primer. The 8 bases at the 5' end consist of 6 bases to be peeled back and two stop bases. Symmetric primers (a pair of forward and reverse primers ending in the same 6 bases and therefore producing the same overhang) and asymmetric primers (a pair of forward and reverse primers ending a different sequence of 6 bases and therefore producing different overhangs) are chosen.

PCR Amplification

Targets are amplified with Phusion II polymerase according to the manufacturer's recommendations using either a symmetric primer pair or an asymmetric primer pair, before being purified by AMPURE SPRI beads.

T4 Peel Back

Purified PCR products are treated by T4 DNA polymerase with DTT, Buffer 2 (New England Biosciences, Inc.), BSA, and the base complementary to the stop base before being heat inactivated and purified with a QiaQuick® spin column.

Ligation

Purified T4 products are ligated with T4 or T7 ligase with Pacific Biosciences of California, Inc. Template Prep Buffer and ATP Low and adapters with the appropriate overhang before being heat inactivated. Symmetric products were ligated to the C2 adapter (to produce a symmetric SMRTBELL circular nucleic acid template). Asymmetric products were ligated to the C2 adapter with one overhang and an scr adapter with the other overhang (to produce an asymmetric SMRTBELL circular nucleic acid template).

DNA Damage Repair

Heat inactivated samples are treated with Pacific Biosciences of California, Inc. Template Prep Buffer, NAD+, ATP High, dNTP, and DNA Damage Repair mix.

Exo Treatment

Repaired Template Mix was treated with ExoIII and ExoVII before being AMPURE SPRI bead purified.

Primer Annealing

Symmetric SMRTBELL circular nucleic acid templates are annealed to Pacific Biosciences of California, Inc. C2v2 Primer (complementary to C2 adapter sequence) in Primer Buffer. Asymmetric SMRTBELL circular nucleic acid templates are annealed to C2v2 Primer (complementary to C2 adapter sequence) and capture hook (complementary to scr adapter sequence but with no free 3' end for polymerase to extend from; can assist with subsequent magbead loading, see, e.g., U.S. Pat. No. 8,658,364).

iTube Formation and Sequencing

Annealed SMRTBELL circular nucleic acid templates are complexed with Pacific Biosciences of California, Inc. P6 enzyme according to the manufacturer's recommendations and run on the PacBio® RS II SMRT® DNA sequencing system with magbead loading and C4 chemistry.

Results

Figure 6:
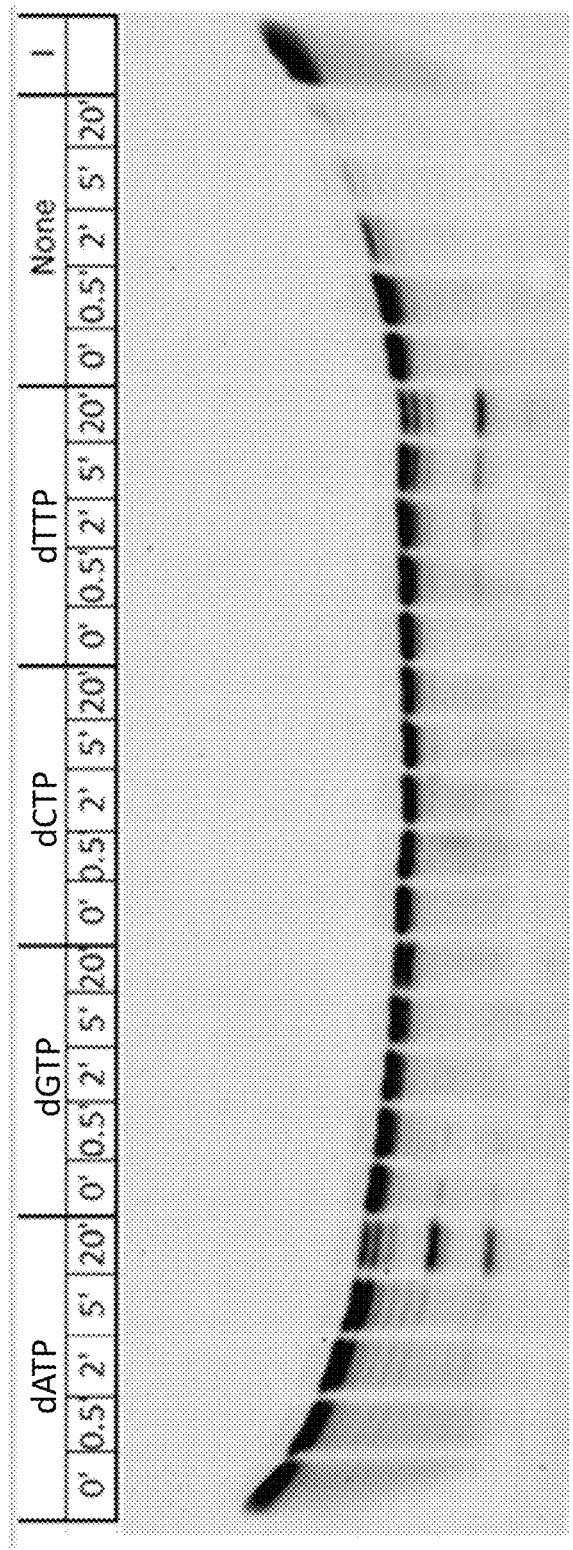
FIG. 6 presents data from an experiment in which a labeled double-stranded oligo is treated with T4 polymerase in the presence of the indicated nucleotide for the indicated time. The lane of the gel labeled "I" includes the initial labeled double-stranded oligo, without any treatment.

An initial experiment demonstrates that the exonuclease activity of T4 polymerase can be used to peel back one strand of a double-stranded nucleic acid to produce a single-stranded overhang. A 5' labeled 30-mer (SEQ ID NO:1, FIG. 6) was duplexed with its unlabeled complement before being treated with T4 polymerase in the presence of a single type of nucleotide. As shown in FIG. 6, exonuclease peel back is observed to the base complementary to the particular nucleotide that is added. The exonuclease usually stops at the first complementary base, but some peel back to the second or third complementary base is observed. Without any nucleotide present, the template is completely degraded by the T4 polymerase.

Figure 7:
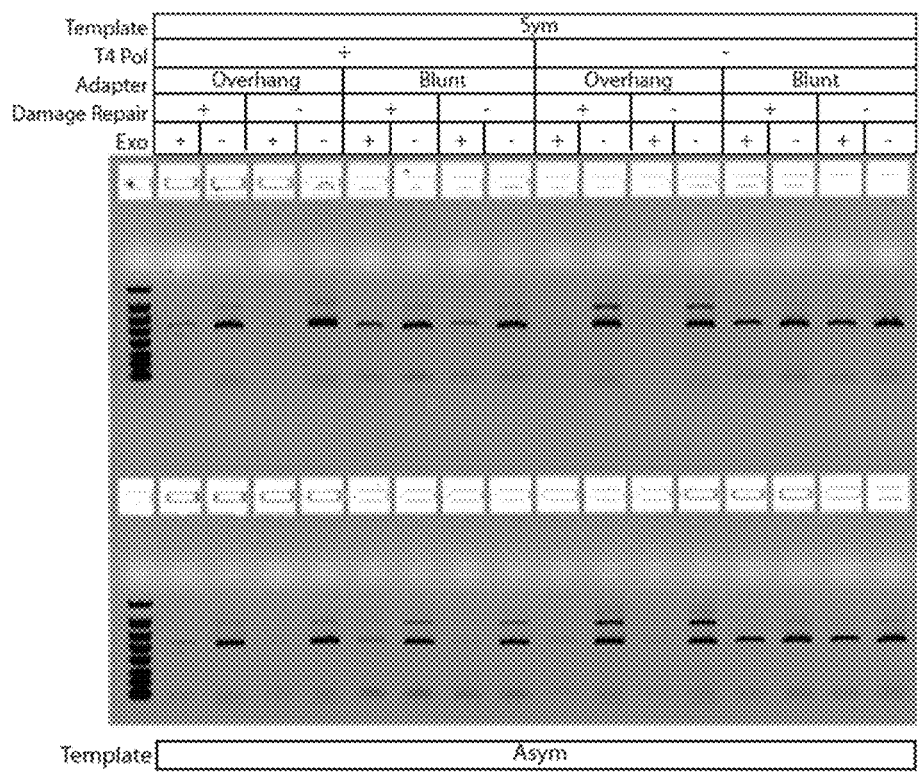
FIG. 7 presents data illustrating that, where exonuclease trimming by T4 polymerase is employed to create sticky ends on a PCR product, proper SMRTBELL circular nucleic acid template production after ligation with sticky adapters is dependent on T4 activity.

The results shown in FIG. 7 demonstrate that sticky ends formed by T4 polymerase can be used to produce SMRTBELL circular nucleic acid templates. Symmetric (top lanes) and asymmetric (bottom lanes) PCR products were produced; treated with T4 polymerase and a nucleotide complementary to the stop base (left lanes) or not treated (right lanes); incubated with ligase and either sticky ended (overhang) or blunt ended adapters; treated with damage repair mix or not treated; and then treated with exonuclease or not treated. Proper SMRTBELL circular nucleic acid template formation with the sticky ended adapters is dependent on T4 polymerase activity. DNA damage repair appears to improve SMRTBELL circular nucleic acid template yield. Without limitation to any particular mechanism, damage repair may fill in gaps produced when T4's exonuclease activity sometimes proceeds further than desired or where the 6 bp overhangs on the product and adapter occasionally misalign with each other. SMRTBELL circular nucleic acid templates are observed as expected with blunt ended adapters in the absence of T4 polymerase treatment. SMRTBELL circular nucleic acid formation is also seen with blunt adapters and T4 treated samples, likely due to incomplete exonuclease activity of the T4 polymerase.

Figure 8A:
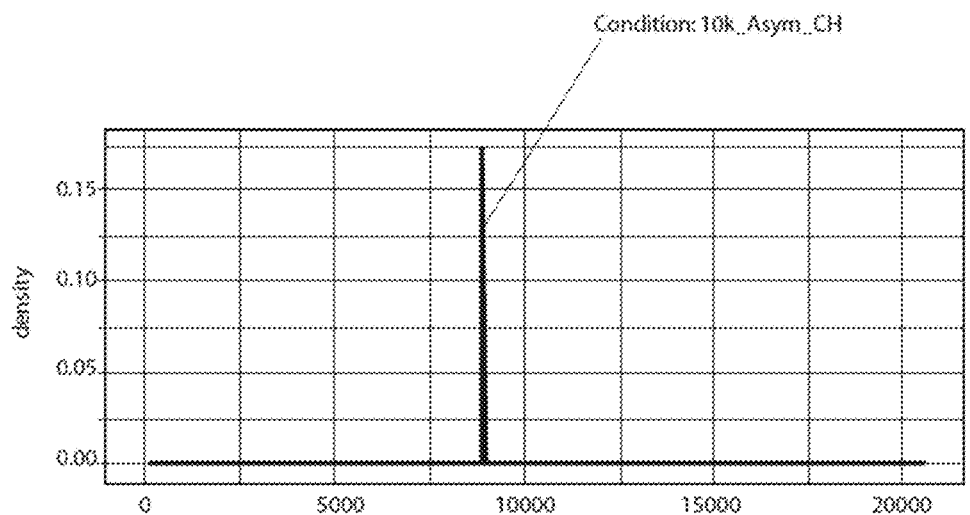
FIG. 8A shows the single sequencing start position observed for an asymmetric SMRTBELL circular nucleic acid template.
Figure 8B:
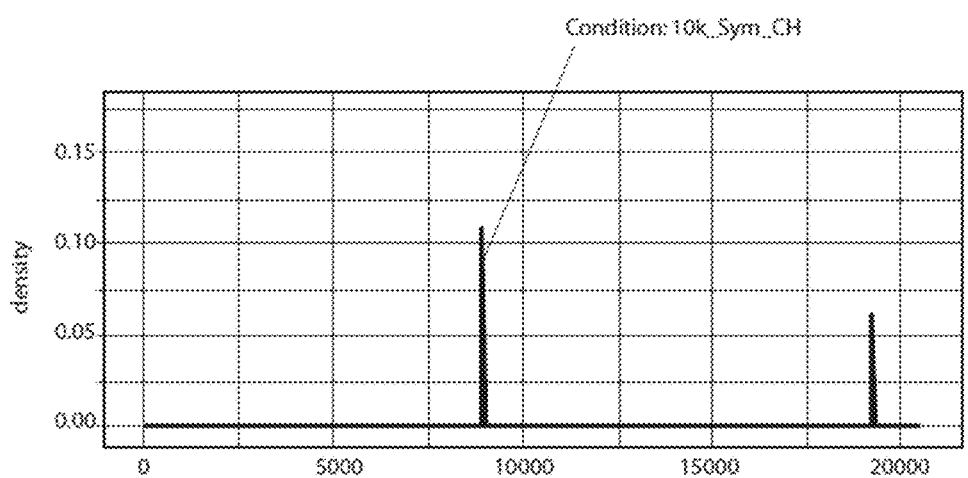
FIG. 8B shows the two sequencing start positions observed for a symmetric SMRTBELL circular nucleic acid template.

Templates prepared using T4 polymerase's exonuclease activity to form sticky ends for ligation to complementary adapters behave as expected when sequenced. A target approximately 10,000 nt long is amplified with symmetric or asymmetric primers and treated as described above to produce a product with symmetric or asymmetric overhangs. Symmetric and asymmetric SMRTBELL circular nucleic acid templates are prepared by ligation to a single adapter or two different adapters, respectively, and then sequenced. Reads that start in the first 30 sec of the movie are analyzed for their start position and plotted against the unrolled template sequence. As shown in FIG. 8B, the symmetric template shows two start positions, corresponding to the two identical C2 adapters (which both contain a binding site for the sequencing primer). As shown in FIG. 8A, the asymmetric template shows only a single start position, corresponding to the C2 adapter.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

sequences anneal to sites in the nucleic acid that flank the target region on opposite strands, and wherein the forward and reverse internal primers are 5' blocked;

subjecting the amplification mixture to amplification to produce a mixture of nucleic acid products; and selectively degrading those nucleic acid products in the product mixture into which both a forward external primer and a reverse external primer were not incorporated, wherein the nucleic acid product into which both a forward external primer and a reverse external primer were incorporated is protected from degradation.

2. The method of claim 1, wherein ligation of two stem-loop adapters to the nucleic acid product into which both a forward external primer and a reverse external primer were incorporated protects it from degradation.

3. The method of claim 2, wherein selectively degrading those nucleic acid products into which both a forward external primer and a reverse external primer were not incorporated comprises treating the product mixture with one or more exonucleases to digest nucleic acid products having one or no stem-loop adapter ligated thereto.

4. The method of claim 2, comprising determining a polynucleotide sequence of the target region, the first tag sequence, and the optional second tag sequence.

5. The method of claim 1, comprising preparing multiple amplification mixtures;

wherein different amplification mixtures comprise a nucleic acid comprising the same target region from different sources; the same forward and reverse internal primers; and forward and reverse external primers comprising the same first and second universal sequences but different first and optional second tag sequences, which first and optional second tag sequences uniquely identify the source for each of the nucleic acids; and subjecting the amplification mixtures to amplification.

What is claimed is:

1. A method for amplifying and tagging a target nucleic acid, the method comprising:

preparing an amplification mixture comprising a nucleic acid comprising a target region, a forward internal primer comprising a first universal sequence and a first target-specific sequence, a reverse internal primer comprising a second universal sequence and a second target-specific sequence, a forward external primer comprising the first universal sequence and a first tag sequence, and a reverse external primer comprising the second universal sequence and an optional second tag sequence, wherein the first and second target-specific 6. The method of claim 5, comprising, after subjecting the amplification mixtures to amplification, pooling the resulting mixtures of nucleic acid products to provide a pooled product mixture, and selectively degrading those nucleic acid products in the pooled product mixture into which both a forward external primer and a reverse external primer were not incorporated.

7. The method of claim 1, wherein the reverse external primer comprises a second tag sequence.

8. The method of claim 7, wherein the first and second tag sequences comprise different polynucleotide sequences.

9. The method of claim 1, wherein the first and second universal sequences comprise different polynucleotide sequences.

10. A method for amplifying and tagging a target nucleic acid, the method comprising:
preparing a first amplification mixture comprising a nucleic acid comprising a target region, a forward internal primer comprising a first universal sequence and a first target-specific sequence, and a reverse internal primer comprising a second universal sequence and a second target-specific sequence, wherein the first and second target-specific sequences anneal to sites in the nucleic acid that flank the target region on opposite strands, and wherein the forward and reverse internal primers are 5' blocked;
subjecting the first amplification mixture to amplification to produce a 5' blocked intermediate product;
preparing a second amplification mixture comprising the intermediate product, a forward external primer comprising the first universal sequence and a first tag sequence, and a reverse external primer comprising the second universal sequence and an optional second tag sequence;
subjecting the second amplification mixture to amplification to produce a tagged product;
ligating two stem-loop adapters to the ends of the tagged product to produce a circular nucleic acid; and
exposing the circular nucleic acid to one or more exonucleases, wherein the one or more exonucleases selectively degrade any single-stranded or non-circular double-stranded nucleic acid present but do not degrade the circular nucleic acid.

11. The method of claim 10, comprising determining a polynucleotide sequence of the target region, the first tag sequence, and the optional second tag sequence.

12. The method of claim 10, comprising preparing multiple first and second amplification mixtures; wherein different first amplification mixtures comprise a nucleic acid comprising the same target region from different sources and the same forward and reverse internal primers; wherein different second amplification mixtures comprise forward and reverse external primers comprising the same first and second universal sequences but different first and optional second tag sequences, which first and optional second tag sequences uniquely identify the source for each of the nucleic acids.

13. The method of claim 12, comprising, after subjecting the first and second amplification mixtures to amplification, pooling the resulting tagged products prior to the ligating step.

14. The method of claim 10, wherein the reverse external primer comprises a second tag sequence.

15. The method of claim 14, wherein the first and second tag sequences comprise different polynucleotide sequences.

16. The method of claim 10, wherein the first and second universal sequences comprise different polynucleotide sequences.

* * * * *